(12) United States Patent (10) Patent No.: US 8,244,347 B2
Lozano (45) Date of Patent: Aug. 14, 2012

(54) METHODS AND APPARATUS FOR EFFECTUATING A LASTING CHANGE IN A NEURAL FUNCTION OF A PATIENT, INCLUDING VIA MECHANICAL FORCE ON NEURAL TISSUE

(75) Inventor: Andres M. Lozano, Toronto (CA)

(73) Assignee: Andres M. Lozano, Toronto (CA)

( * ) Notice: Subject to any disclaimer, the term of this patent is extended or adjusted under 35 U.S.C. 154(b) by 1016 days.

(21) Appl. No.: 11/885,540

(22) PCT Filed: Mar. 6, 2006

(86) PCT No.: PCT/CA2006/000317
§ 371 (c)(1),
(2), (4) Date: Jun. 3, 2008

(87) PCT Pub. No.: WO2006/092061
PCT Pub. Date: Sep. 8, 2006

(65) Prior Publication Data
US 2008/0275526 A1 Nov. 6, 2008

Related U.S. Application Data

(60) Provisional application No. 60/658,888, filed on Mar. 4, 2005.

(51) Int. Cl.
*A61N 1/00* (2006.01)
(52) U.S. Cl. .......................................................... 607/3
(58) Field of Classification Search .................. 607/2, 3, 607/45
See application file for complete search history.

(56) References Cited

U.S. PATENT DOCUMENTS

| 4,062,354 A | | 12/1977 | Taylor |
| 4,658,835 A | | 4/1987 | Pohndorf |
| 5,558,617 A | * | 9/1996 | Heilman et al. ............... 600/16 |
| 5,575,813 A | | 11/1996 | Edell et al. |
| 6,540,659 B1 | * | 4/2003 | Milbocker ..................... 600/17 |
| 7,300,449 B2 | * | 11/2007 | Mische ........................ 606/198 |
| 7,684,866 B2 | * | 3/2010 | Fowler et al. .................. 607/45 |
| 2006/0036126 A1 | * | 2/2006 | Ross et al. ...................... 600/16 |
| 2010/0036452 A1 | * | 2/2010 | Gluckman et al. ............. 607/45 |

OTHER PUBLICATIONS

International Search Report from PCT/CA2006/000317, dated Jun. 1, 2006.

* cited by examiner

*Primary Examiner* — Scott Getzow
(74) *Attorney, Agent, or Firm* — Sim & McBurney

(57) ABSTRACT

Methods and apparatus for effectuating a lasting change in a neural function of a patient, including via mechanical force on neural tissue, are disclosed. An apparatus in accordance with one embodiment includes an implantable force delivery device that is changeable between a first state in which the force delivery device applies a first mechanical force to neural tissue, and the second state in which the force delivery device applies no mechanical force or a second mechanical force less than the first mechanical force to the neural tissue, while the force delivery device is implanted. An actuator can be coupled to the force delivery device with a communication link to change the state of the force delivery device, and a controller can be operably coupled to the actuator to automatically direct the force delivery device to change repeatedly between the first and second states while the force delivery device is implanted.

55 Claims, 29 Drawing Sheets

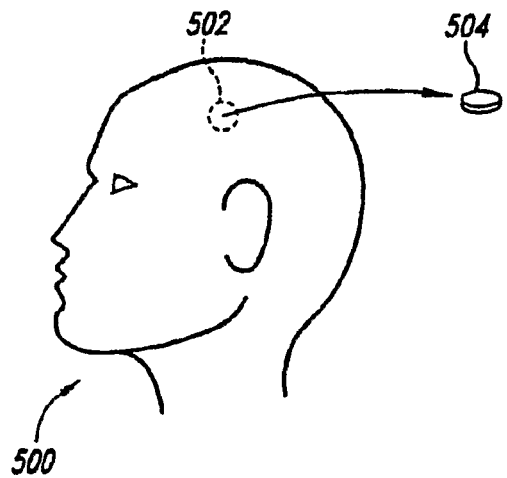
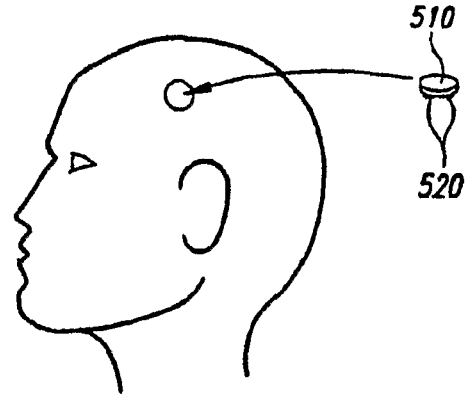
Fig. 5A
Fig. 5B
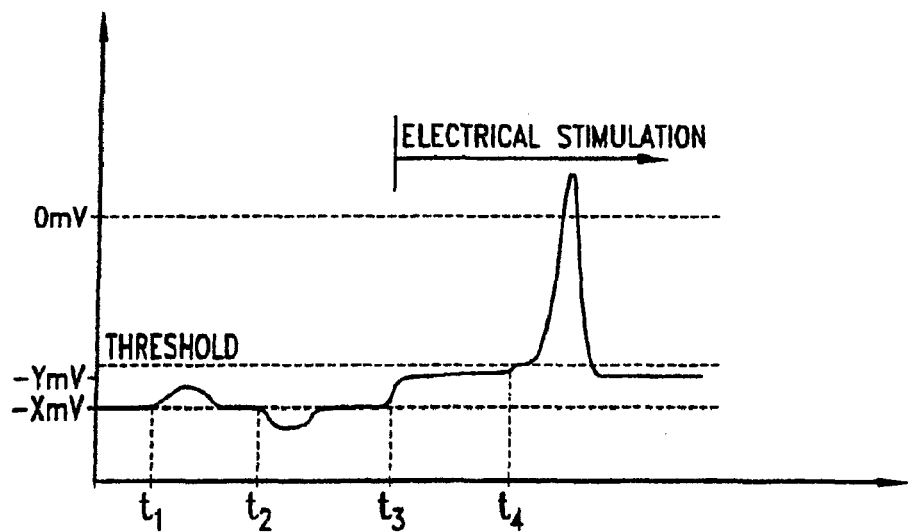
Fig. 5C

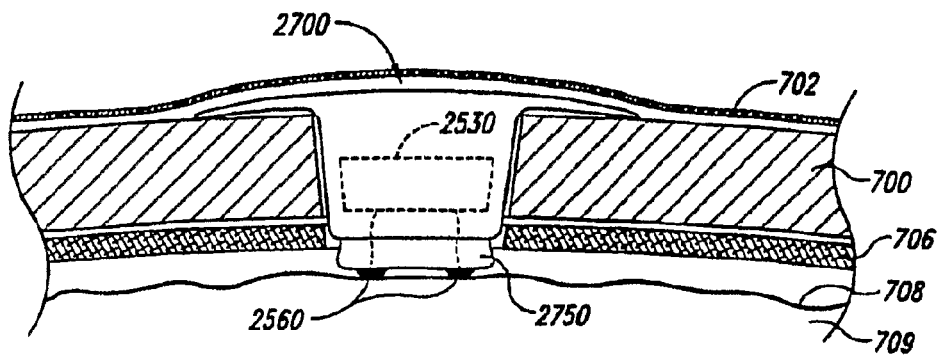
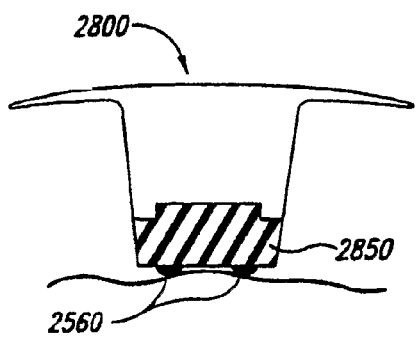
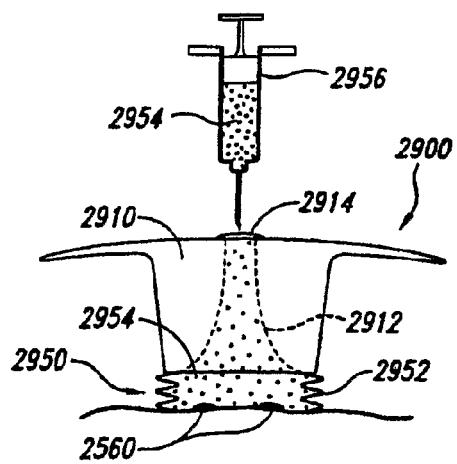
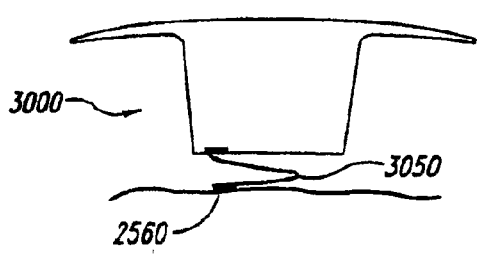

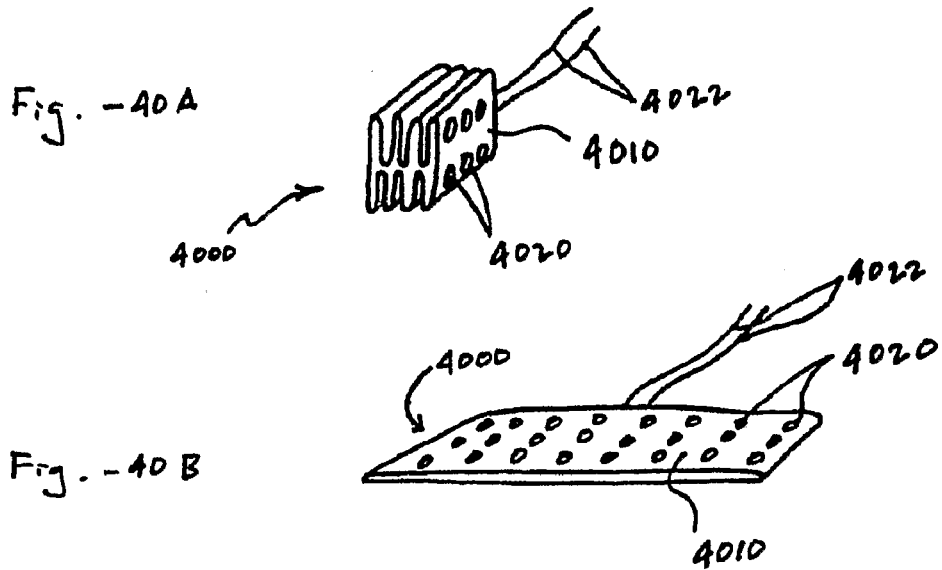
Fig. -40A
Fig. -40B
Fig. -41A
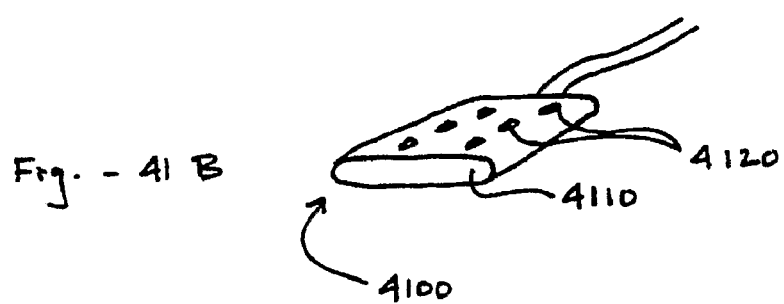
Fig. -41B

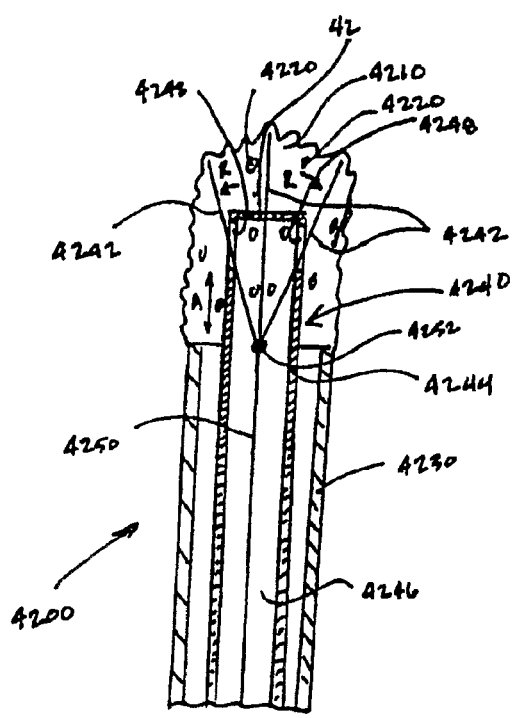
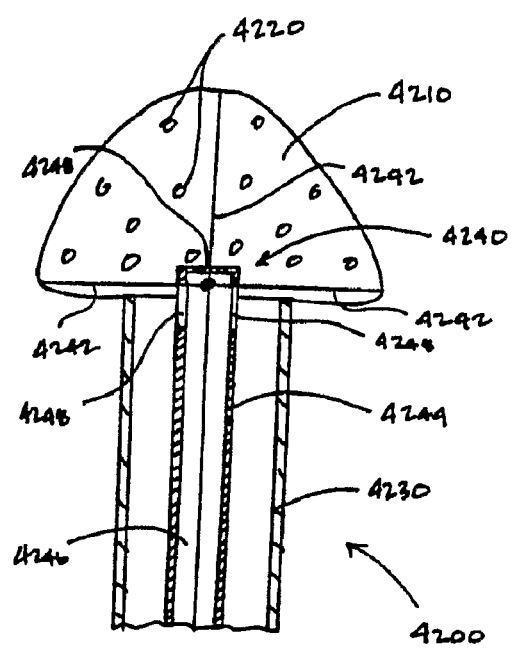
Fig. - 42 A
Fig. - 42 B

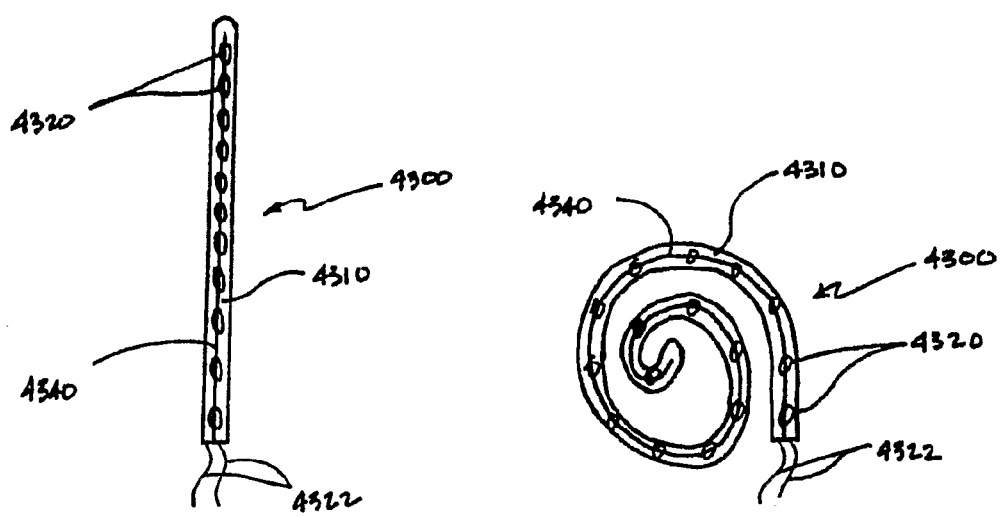
Fig. —43A    Fig. —43B

| Indication Treatment of | Brain Target |
|---|---|
| Auditory Hallucinations and schizophrenia | Auditory pathways and cortex |
| Epilepsy | Seizure focus identified with EEG, PET, SPECT, |
| Tourette's | Cortical Surface premotor cortex- PMC, Supplementary motor cortex- SMA, motor cortex, Motor Thalamus, Pallidum |
| Depression/Mood disorder | Orbital frontal Cortex<br>Prefrontal Cortex<br>Dorsolateral prefrontal cortex |
| Stuttering | Cortical surface- Motor, premotor area, Motor Thalamus, Pallidum |
| Writer's cramp | Motor cortex somatotopically, PMC, SMA, Motor Thalamus, Palllidum |
| Focal Dystonia | Motor cortex somatotopically, PMC, SMA, Motor thalamus, Pallidum Brodmannn area 6 and 40/7 |
| Generalized Dystonia | Motor cortex somatotopically, PMC, SMA, Motor thalamus, Pallidum, Brodmann area 6 and 40/7 |
| Myoclonus | Motor cortex somatotopically, PMC, SMA, Motor thalamus, Pallidum |
| Chorea/hemibalism | Motor cortex somatotopically, PMC, SMA, Motor thalamus, Pallidum |
| Cerebellar tremor/Holmes tremor/tremor with Multiple sclerosis/post traumatic and post-stroke tremor, Essential tremor | Cerebellar surface, Cerebellar peduncles, Motor Thalamus |
| Attention Deficit/Hyperactivity Disorder | Frontal and prefrontal cortical surface |
| Drug dependence, alcohol, nicotine, cocaine, opiates, other stimulants | Cortical and subcortical projections to Nucleus accumbens, Nucleus accumbens per se, Ventral Tegmental area, |
| Eating Disorders/Obesity | Cortical and subcortical projections to Nucleus accumbens, Nucleus accumbens per se, Ventral Tegmental area, |
| Pain- deafferentation and nociceptive. | fMRI and PET driven patient and target selection, Cingulate Gyrus, Insula Secondary Somatosensory Cortex Motor Cortex |

FIG. 51

METHODS AND APPARATUS FOR EFFECTUATING A LASTING CHANGE IN A NEURAL FUNCTION OF A PATIENT, INCLUDING VIA MECHANICAL FORCE ON NEURAL TISSUE

CROSS-REFERENCE TO RELATED APPLICATION

This application claims the benefit of U.S. Application No. 60/658,888 filed on Mar. 4, 2005.

TECHNICAL FIELD

Several embodiments of methods and apparatus in accordance with the invention are related to effectuating a lasting change in a neural function of a patient, including via mechanical force on neural tissue.

BACKGROUND

A wide variety of mental and physical processes are known to be controlled or are influenced by neural activity in particular regions of the brain. In some areas of the brain, such as in the sensory or motor cortices, the organization of the brain resembles a map of the human body; this is referred to as the "somatotopic organization of the brain." There are several other areas of the brain that appear to have distinct functions that are located in specific regions of the brain in most individuals. For example, areas of the occipital lobes relate to vision, regions of the left inferior frontal lobes relate to language in the majority of people, and regions of the cerebral cortex appear to be consistently involved with conscious awareness, memory, and intellect. This type of location-specific functional organization of the brain, in which discrete locations of the brain are statistically likely to control particular mental or physical functions in normal individuals, is herein referred to as the "functional organization of the brain."

Many problems or abnormalities with body functions can be caused by damage, disease and/or disorders of the brain. A stroke, for example, is one very common condition that damages the brain. Strokes are generally caused by emboli (e.g., obstruction of a vessel), hemorrhages (e.g., rupture of a vessel), or thrombi (e.g., clotting) in the vascular system of a specific region of the cortex, which in turn generally causes a loss or impairment of a neural function (e.g., neural functions related to face muscles, limbs, speech, etc.). Stroke patients are typically treated using physical therapy to rehabilitate the loss of function of a limb or another affected body part. For most patients, little can be done to improve the function of the affected limb beyond the recovery that occurs naturally without intervention. One existing physical therapy technique for treating stroke patients constrains or restrains the use of a working body part of the patient to force the patient to use the affected body part. For example, the loss of use of a limb is treated by restraining the other limb. Although this type of physical therapy has shown some experimental efficacy, it is expensive, time-consuming and little-used. Stroke patients can also be treated using physical therapy plus adjunctive therapies. For example, some types of drugs, such as amphetamines, that increase the activation of neurons in general, appear to enhance neural networks; these drugs, however, have limited efficacy because they are very non-selective in their mechanisms of action and cannot be delivered in high concentrations directly at the site where they are needed.

Therefore, there is a need to develop effective treatments for rehabilitating stroke patients and patients that have other types of brain damage.

Other brain disorders and diseases are also difficult to treat. Alzheimer's disease, for example, is known to affect portions of the cortex, but the cause of Alzheimer's disease and how it alters the neural activity in the cortex is not fully understood. Similarly, the neural activity of brain disorders (e.g., depression and obsessive-compulsive behavior) is also not fully understood. Therefore, there is also a need to develop more effective treatments for other brain disorders and diseases.

The neural activity in the brain can be influenced by electrical energy that is supplied from an external source outside of the body. Various neural functions can thus be promoted or disrupted by applying an electrical current to the cortex or other region of the brain. As a result, the quest for treating damage, disease and disorders in the brain have led to research directed toward using electricity or magnetism to control brain functions.

One type of treatment is transcranial electrical stimulation (TES), which involves placing an electrode on the exterior of the scalp and delivering an electrical current to the brain through the scalp and skull. Patents directed to TES include: U.S. Pat. No. 5,540,736 issued to Haimovich et al. (for providing analgesia); U.S. Pat. No. 4,140,133 issued to Katrubin et al. (for providing anesthesia); U.S. Pat. No. 4,646,744 issued to Capel (for treating drug addiction, appetite disorders, stress, insomnia and pain); and U.S. Pat. No. 4,844,075 issued to Liss et al. (for treating pain and motor dysfunction associated with cerebral palsy). TES, however, is not widely used because the patients experience a great amount of pain and the electrical field is difficult to direct or focus accurately.

Another type of treatment is transcranial magnetic stimulation (TMS), which involves producing a high-powered magnetic field adjacent to the exterior of the scalp over an area of the cortex. TMS does not cause the painful side effects of TES. Since 1985, TMS has been used primarily for research purposes in brain-mapping endeavors. Recently, however, potential therapeutic applications have been proposed primarily for the treatment of depression. A small number of clinical trials have found TMS to be effective in treating depression when used to stimulate the left prefrontal cortex.

The TMS treatment of a few other patient groups have been studied with promising results, such as patients with Parkinson's disease and hereditary spinocerebellar degeneration. Patents and published patent applications directed to TMS include: published international patent application WO 98/06342 (describing a transcranial magnetic stimulator and its use in brain mapping studies and in treating depression); U.S. Pat. No. 5,885,976 issued to Sandyk (describing the use of transcranial magnetic stimulation to treat a variety of disorders allegedly related to deficient serotonin neurotransmission and impaired pineal melatonin functions); and U.S. Pat. No. 5,092,835 issued to Schurig et al. (describing the treatment of neurological disorders (such as autism), treatment of learning disabilities, and augmentation of mental and physical abilities of "normal" people by a combination of transcranial magnetic stimulation and peripheral electrical stimulation).

Independent studies have also demonstrated that TMS is able to produce a lasting change in neural activity within the cortex that occurs for a period of time after terminating the TMS treatment ("neuroplasticity"). For example, Ziemann et al., *Modulation of Plasticity in Human Motor Cortex after Forearm Ischemic Nerve Block*, 18 J Neuroscience 1115 (February 1998), disclose that TMS at subthreshold levels (e.g., levels at which movement was not induced) in neuro-block models that mimic amputation was able to modify the lasting changes in neural activity that normally accompany amputation. Similarly, Pascual-Leone et al. (submitted for publication) disclose that applying TMS over the contralateral motor cortex in normal subjects who underwent immobilization of a hand in a cast for 5 days can prevent the decreased motor cortex excitability normally associated with immobilization. Other researchers have proposed that the ability of TMS to produce desired changes in the cortex may someday be harnessed to enhance neuro-rehabilitation after a brain injury, such as stroke, but there are no published studies to date.

Other publications related to TMS include Cohen et al., *Studies of Neuroplasticity With Transcranial Magnetic Stimulation,* 15 J. Clin. Neurophysiol. 305 (1998); Pascual-Leone et al., *Transcranial Magnetic Stimulation and Neuroplasticity,* 37 Neuropsychologia 207 (1999); Stefan et al., *Induction of Plasticity in the Human Motor Cortex by Paired Associative Stimulation,* 123 Brain 572 (2000); Sievner et al., *Lasting Cortical Activation after repetitive TMS of the Motor Cortex,* 54 Neurology 956 (February 2000); Pascual-Leone et al., *Study and Modulation of Human Cortical Excitability With Transcranial Magnetic Stimulation,* 15 J. Clin. Neurophysiol. 333 (1998); and Boylan et al., *Magnetoelectric Brain Stimulation in the Assessment Of Brain Physiology And Pathophysiology,* 111 Clin. Neurophysiology 504 (2000).

Although TMS appears to be able to produce a change in the underlying cortex beyond the time of actual stimulation, TMS is not presently effective for treating many patients because the existing delivery systems are not practical for applying stimulation over an adequate period of time. TMS systems, for example, are relatively complex and require stimulation treatments to be performed by a healthcare professional in a hospital or physician's office. TMS systems also may not be reliable for longer-term therapies because it is difficult to (a) accurately localize the region of stimulation in a reproducible manner, and (b) hold the device in the correct position over the cranium for a long period, especially when a patient moves or during rehabilitation. Furthermore, current TMS systems generally do not sufficiently focus the electromagnetic energy on the desired region of the cortex for many applications. As such, the potential therapeutic benefit of TMS using existing equipment is relatively limited.

Direct and indirect electrical stimulation of the central nervous system has also been proposed to treat a variety of disorders and conditions. For example, U.S. Pat. No. 5,938,688 issued to Schiff notes that the phenomenon of neuroplasticity may be harnessed and enhanced to treat cognitive disorders related to brain injuries caused by trauma or stroke. Schiff's implant is designed to increase the level of arousal of a comatose patient by stimulating deep brain centers involved in consciousness. To do this, Schiffs invention involves electrically stimulating at least a portion of the patient's intralaminar nuclei (i.e., the deep brain) using, e.g., an implantable multipolar electrode and either an implantable pulse generator or an external radiofrequency controlled pulse generator. Schiff's deep brain implant is highly invasive, however, and could involve serious complications for the patient.

Likewise, U.S. Pat. No. 6,066,163 issued to John acknowledges the ability of the brain to overcome some of the results of an injury through neuroplasticity. John also cites a series of articles as evidence that direct electrical stimulation of the brain can reverse the effects of a traumatic injury or stroke on the level of consciousness. The system disclosed in John stimulates the patient and modifies the parameters of stimulation based upon the outcome of comparing the patient's present state with a reference state in an effort to optimize the results. Like Schiff, however, the invention disclosed in John is directed to a highly invasive deep brain stimulation system.

Another device for stimulating a region of the brain is disclosed by King in U.S. Pat. No. 5,713,922. King discloses a device for cortical surface stimulation having electrodes mounted on a paddle implanted under the skull of the patient. The electrodes are implanted on the surface of the brain in a fixed position. The electrodes in King accordingly cannot move to accommodate changes in the shape of the brain. King also discloses that the electrical pulses are generated by a pulse generator that is implanted in the patient remotely from the cranium (e.g., subclavicular implantation). The pulse generator is not directly connected to the electrodes, but rather it is electrically coupled to the electrodes by a cable that extends from the remotely implanted pulse generator to the electrodes implanted in the cranium. The cable disclosed in King extends from the paddle, around the skull, and down the neck to the subclavicular location of the pulse generator.

King discloses implanting the electrodes in contact with the surface of the cortex to create paresthesia, which is a sensation of vibration or "buzzing" in a patient. More specifically, King discloses inducing paresthesia in large areas by applying electrical stimulation to a higher element of the central nervous system (e.g., the cortex). As such, King discloses placing the electrodes against particular regions of the brain to induce the desired paresthesia. The purpose of creating paresthesia over a body region is to create a distracting stimulus that effectively reduces perception of pain in the body region. Thus, King appears to require stimulation above activation levels.

Although King discloses a device that stimulates a region on the cortical surface, this device is expected to have several drawbacks. First, it is expensive and time-consuming to implant the pulse generator and the cable in the patient. Second, it appears that the electrodes are held at a fixed elevation that does not compensate for anatomical changes in the shape of the brain relative to the skull, which makes it difficult to accurately apply an electrical stimulation to a desired target site of the cortex in a focused, specific manner. Third, King discloses directly activating the neurons to cause paresthesia, which is not expected to cause entrainment of the activity in the stimulated population of neurons with other forms of therapy or adaptive behavior, such as physical or occupational therapy. Thus, King is expected to have several drawbacks.

King and the other foregoing references are also expected to have drawbacks in producing the desired neural activity because these references generally apply the therapy to the region of the brain that is responsible for the physiological function or mental process according to the functional organization of the brain. In the case of a brain injury or disease, however, the region of the brain associated with the affected physiological function or cognitive process may not respond to stimulation therapies. Thus, existing techniques may not produce adequate results that last beyond the stimulation period.

In some cases, retraction of part of the brain is used in neurosurgical procedures, e.g., to reach certain brain areas or for device implantation procedures. Prior studies have indicated that forces applied intermittently via retraction may not create damage (see J. Neurosurg. 1983 June: 58(6):918-23, "Intermittent versus continuous brain retraction: An experimental study" by Yokoh A., Sugita K., Kobayashi S.). This article reports that brain damage due to retraction was studied morphologically and physiologically in the dog brain. Two methods of retraction were compared using a retractor with a strain gauge: 1) continuous retraction; and 2) intermittent retraction. Total retraction time was 60 minutes for each method. Brain damage started to appear at a retraction force of 30 gm with continuous retraction, and increased in proportion to the force used. The power spectrum of the electrocorticogram showed full recovery after the release of retraction when the retraction force was less than 40 gm. With intermittent retraction, the damage was morphologically minimal with a retraction force of less than 50 gm, and recovery of the power spectrum of the electrocorticogram was prompt in comparison with continuous retraction. According to this article, the results indicate the superiority with respect to safety and tolerability of intermittent over continuous retraction.

BRIEF DESCRIPTION OF THE DRAWINGS

FIGS. 5A and 5B are schematic illustrations of an implanting procedure at a stage of a method in accordance with an embodiment of the invention.

FIG. 5C is a graph illustrating firing an "action potential" associated with stimulated neural activity in accordance with one embodiment of the invention.

FIG. 27 is a cross-sectional view schematically illustrating a part of a stimulation apparatus having a biasing element in accordance with an embodiment of the invention.

FIG. 28 is a cross-sectional view of a stimulation apparatus having a biasing element in accordance with still another embodiment of the invention.

FIG. 29 is a cross-sectional view of a stimulation apparatus having a biasing element in accordance with yet another embodiment of the invention.

FIG. 30 is a cross-sectional view of a stimulation apparatus having a biasing element in accordance with yet another embodiment of the invention.

FIGS. 40A and 40B illustrate an implantable stimulation apparatus in accordance with another embodiment of the invention.

FIGS. 41A and 41B illustrate an implantable stimulation apparatus in accordance with another embodiment of the invention.

FIGS. 42A and 42B illustrate an implantable stimulation apparatus in accordance with another embodiment of the invention.

FIGS. 43A and 43B illustrate an implantable stimulation apparatus in accordance with yet another embodiment of the invention.

FIG. 51 is a table illustrating representative indications and associated target brain locations.

DETAILED DESCRIPTION

Figure 1A:
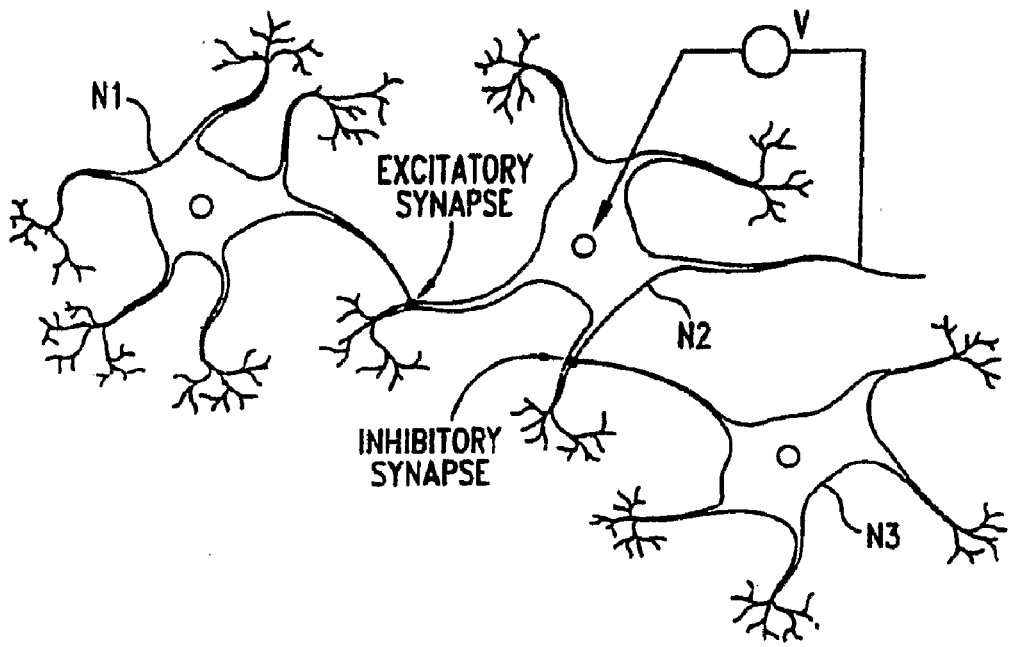
FIG. 1A is a schematic view of neurons.

The following disclosure describes several methods and apparatus for intracranial electrical stimulation to treat or otherwise effectuate a change in neural functions of a patient, including via a mechanical force applied to neural tissue. Several embodiments of methods in accordance with the invention are directed toward enhancing or otherwise inducing neuroplasticity to effectuate a particular neural function. Neuroplasticity refers to the ability of the brain to change or adapt over time. It was once thought adult brains became relatively "hard wired" such that functionally significant neural networks could not change significantly over time or in response to injury. It has become increasingly more apparent that these neural networks can change and adapt over time so that meaningful function can be regained in response to brain injury. An aspect of several embodiments of methods in accordance with the invention is to provide the appropriate triggers for adaptive neuroplasticity. These appropriate triggers appear to cause or enable increased synchrony of functionally significant populations of neurons in a network.

Electrically enhanced or induced neural stimulation in accordance with several embodiments of the invention excites a portion of a neural network involved in a functionally significant task such that a selected population of neurons can become more strongly associated with that network. Because such a network will subserve a functionally meaningful task, such as motor relearning, the changes are more likely to be lasting because they are continually being reinforced by natural use mechanisms. The nature of stimulation in accordance with several embodiments of the invention ensures that the stimulated population of neurons links to other neurons in the functional network. It is expected that this occurs because action potentials are not actually caused by the stimulation, but rather are caused by interactions with other neurons in the network. Several aspects of the electrical stimulation in accordance with selected embodiments of the invention simply allows this to happen with an increased probability when the network is activated by favorable activities, such as rehabilitation or limb use.

The methods in accordance with the invention can be used to treat brain damage (e.g., stroke, trauma, etc.), brain disease (e.g., Alzheimer's, Pick's, Parkinson's, etc.), and/or brain disorders (e.g., epilepsy, depression, etc.). The methods in accordance with the invention can also be used to enhance functions of normal, healthy brains (e.g., learning, memory, etc.), or to control sensory functions (e.g., pain).

Certain embodiments of methods in accordance with the invention electrically stimulate the brain at a stimulation site where neuroplasticity is occurring. The stimulation site may be different than the region in the brain where neural activity is typically present to perform the particular function according to the functional organization of the brain. In one embodiment in which neuroplasticity related to the neural function occurs in the brain, the method can include identifying the location where such neuroplasticity is present. This particular procedure may accordingly enhance a change in the neural activity to assist the brain in performing the particular neural function. In an alternative embodiment in which neuroplasticity is not occurring in the brain, an aspect is to induce neuroplasticity at a stimulation site where it is expected to occur. This particular procedure may thus induce a change in the neural activity to instigate performance of the neural function. Several embodiments of these methods are expected to produce a lasting effect on the intended neural activity at the stimulation site.

The specific details of certain embodiments of the invention are set forth in the following description and in FIGS. 1A-40 to provide a thorough understanding of these embodiments to a person of ordinary skill in the art. More specifically, several embodiments of methods in accordance with the invention are initially described with reference to FIGS. 1-5C, and then several embodiments of devices for stimulating the cortical and/or deep-brain regions of the brain are described with reference to FIGS. 6-40. A person skilled in the art will understand that the present invention may have additional embodiments, or that the invention can be practiced without several of the details described below.

A. Methods for Electrically Stimulating Regions of the Brain

1. Embodiments of Electrically Enhancing Neural Activity

Figure 1B:
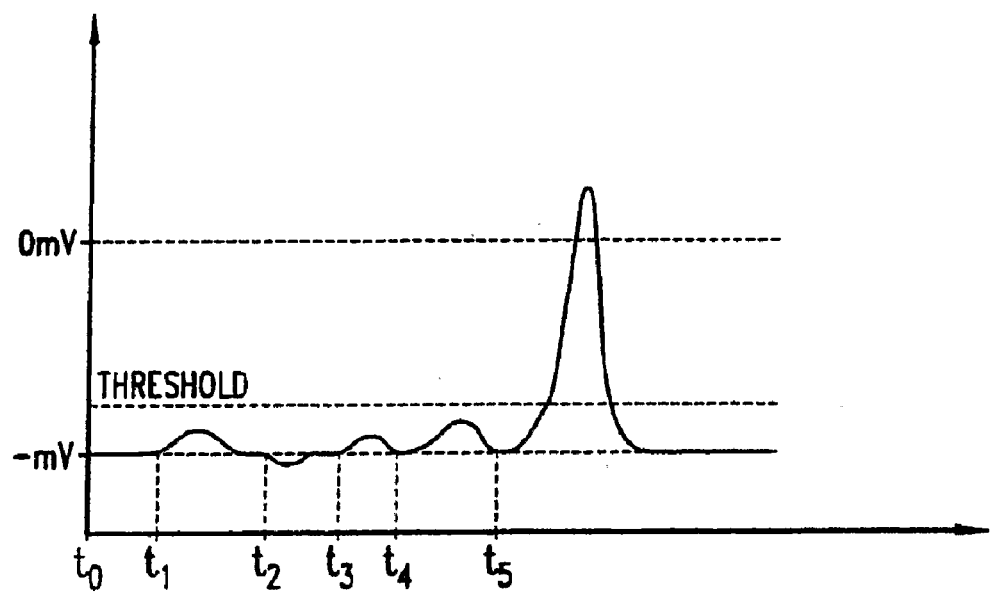
FIG. 1B is a graph illustrating firing an "action potential" associated with normal neural activity.

FIG. 1A is a schematic representation of several neurons N1-N3 and FIG. 1B is a graph illustrating an "action potential" related to neural activity in a normal neuron. Neural activity is governed by electrical impulses generated in neurons. For example, neuron N1 can send excitatory inputs to neuron N2 (e.g., times $t_1$, $t_3$ and $t_4$ in FIG. 1B), and neuron N3 can send inhibitory inputs to neuron N2 (e.g., time $t_2$ in FIG. 1B). The neurons receive/send excitatory and inhibitory inputs from/to a population of other neurons. The excitatory and inhibitory inputs can produce "action potentials" in the neurons, which are electrical pulses that travel through neurons by changing the flux of sodium (Na) and potassium (K)

ions across the cell membrane. An action potential occurs when the resting membrane potential of the neuron surpasses a threshold level. When this threshold level is reached, an "all-or-nothing" action potential is generated. For example, as shown in FIG. 1B, the excitatory input at time $t_5$ causes neuron N2 to "fire" an action potential because the input exceeds the threshold level for generating the action potential. The action potentials propagate down the length of the axon (the long process of the neuron that makes up nerves or neuronal tracts) to cause the release of neurotransmitters from that neuron that will further influence adjacent neurons.

Figure 1C:
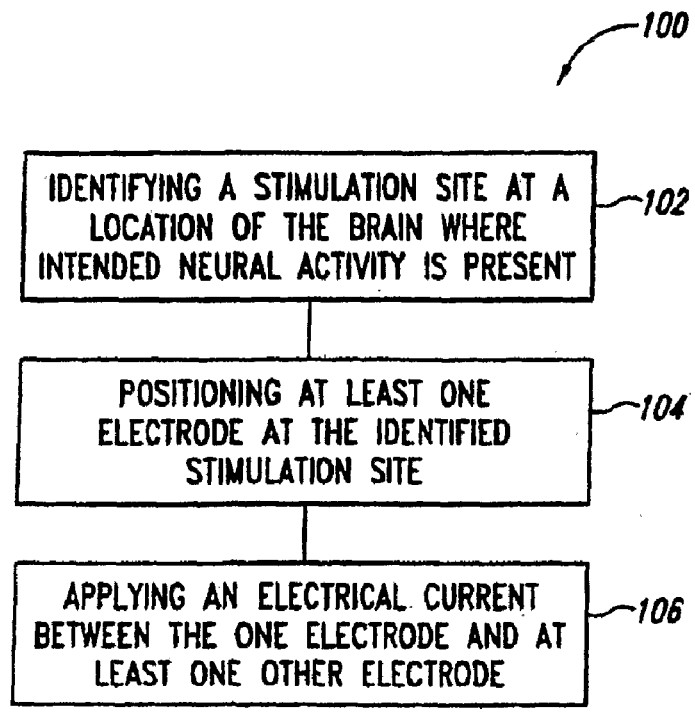
FIG. 1C is a flowchart of a method for effectuating a neural function of a patient associated with a location in the brain in accordance with one embodiment of the invention.

FIG. 1C is a flowchart illustrating a method 100 for effectuating a neural function in a patient in accordance with an embodiment of the invention. The neural function, for example, can control a specific mental process or physiological function, such as a particular motor function or sensory function (e.g., movement of a limb) that is normally associated with neural activity at a "normal" location in the brain according to the functional organization of the brain. In several embodiments of the method 100, at least some neural activity related to the neural function can be occurring at a site in the brain. The site of the neural activity may be at the normal location where neural activity typically occurs to carry out the neural function according to the functional organization of the brain, or the site of the neural activity may be at a different location where the brain has recruited material to perform the neural activity. In either situation, one aspect of several embodiments of the method 100 is to determine the location in the brain where this neural activity is present.

The method 100 includes a diagnostic procedure 102 involving identifying a stimulation site at a location of the brain where an intended neural activity related to the neural function is present. In one embodiment, the diagnostic procedure 102 includes generating the intended neural activity in the brain from a "peripheral" location that is remote from the normal location, and then determining where the intended neural activity is actually present in the brain. In an alternative embodiment, the diagnostic procedure 102 can be performed by identifying a stimulation site where neural activity has changed in response to a change in the neural function. The method 100 continues with an implanting procedure 104 involving positioning first and second electrodes at the identified stimulation site, and a stimulating procedure 106 involving applying an electrical current between the first and second electrodes. Many embodiments of the implanting procedure 104 position two or more electrodes at the stimulation site, but other embodiments of the implanting procedure involve positioning only one electrode at the stimulation site and another electrode remotely from the stimulation site. As such, the implanting procedure 104 of the method 100 can include implanting at least one electrode at the stimulation site. The procedures 102-106 are described in greater detail below.

Figure 2:
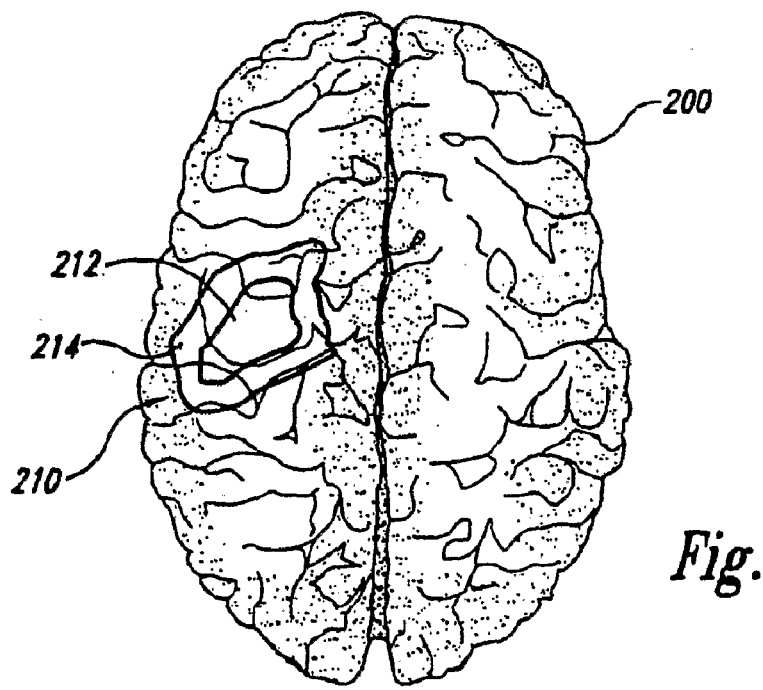
FIG. 2 is a top plan view of a portion of a brain illustrating neural activity in a first region of the brain associated with the neural function of the patient according to the somatotopic organization of the brain.
Figure 3:
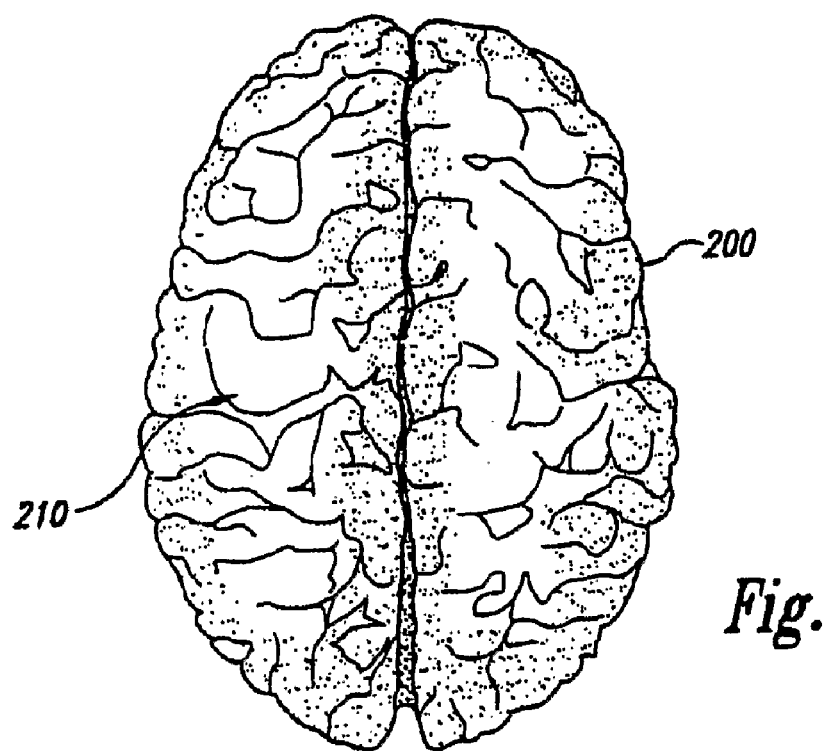
FIG. 3 is a top plan image of a portion of the brain illustrating a loss of neural activity associated with the neural function of the patient used in one stage of a method in accordance with an embodiment of the invention.
Figure 4:
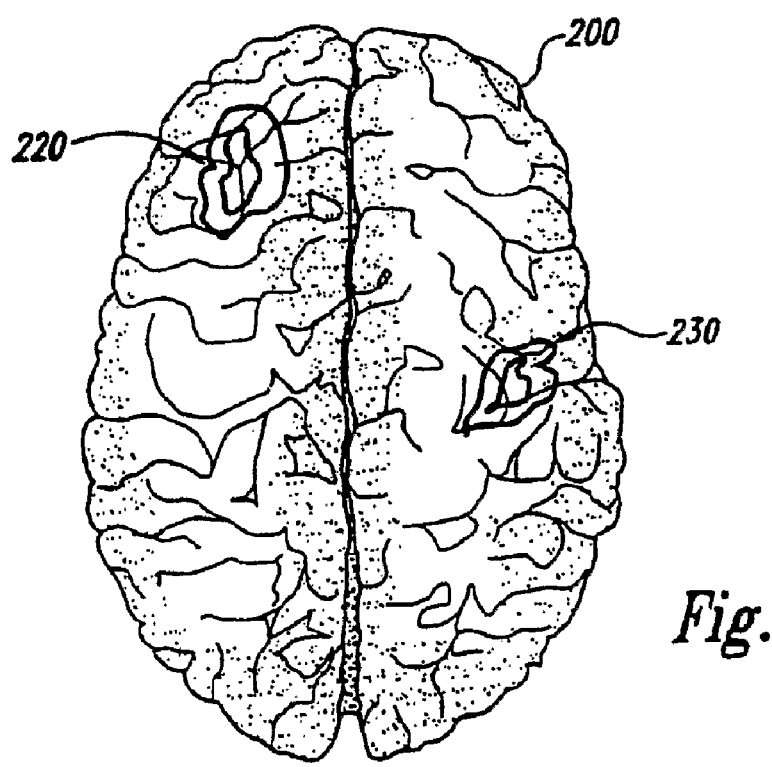
FIG. 4 is a top plan image of the brain of FIG. 3 showing a change in location of the neural activity associated with the neural function of the patient at another stage of a method in accordance with an embodiment of the invention.

FIGS. 2-4 illustrate an embodiment of the diagnostic procedure 102. The diagnostic procedure 102 can be used to determine the region of the brain where stimulation will likely effectuate the desired function, such as rehabilitating a loss of a neural function caused by a stroke, trauma, disease or other circumstance. FIG. 2, more specifically, is an image of a normal, healthy brain 200 having a first region 210 where the intended neural activity occurs to effectuate a specific neural function in accordance with the functional organization of the brain. For example, the neural activity in the first region 210 shown in FIG. 2 is generally associated with the movement of a patient's fingers. The first region 210 can have a high-intensity area 212 and a low-intensity area 214 in which different levels of neural activity occur. It is not necessary to obtain an image of the neural activity in the first region 210 shown in FIG. 2 to carry out the diagnostic procedure 102, but rather it is provided to show an example of neural activity that typically occurs at a "normal location" according to the functional organization of the brain 200 for a large percentage of people with normal brain function. It will be appreciated that the actual location of the first region 210 will generally vary between individual patients.

The neural activity in the first region 210, however, can be impaired. In a typical application, the diagnostic procedure 102 begins by taking an image of the brain 200 that is capable of detecting neural activity to determine whether the intended neural activity associated with the particular neural function of interest is occurring at the region of the brain 200 where it normally occurs according to the functional organization of the brain. FIG. 3 is an image of the brain 200 after the first region 210 has been affected (e.g., from a stroke, trauma or other cause). As shown in FIG. 3, the neural activity that controlled the neural function for moving the fingers no longer occurs in the first region 210. The first region 210 is thus "inactive," which is expected to result in a corresponding loss of the movement and/or sensation in the fingers. In some instances, the damage to the brain 200 may result in only a partial loss of the neural activity in the damaged region. In either case, the image shown in FIG. 3 establishes that the loss of the neural function is related to the diminished neural activity in the first region 210. The brain 200 may accordingly recruit other neurons to perform neural activity for the affected neural function (i.e., neuroplasticity), or the neural activity may not be present at any location in the brain.

FIG. 4 is an image of the brain 200 illustrating a plurality of potential stimulation sites 220 and 230 for effectuating the neural function that was originally performed in the first region 210 shown in FIG. 2. FIGS. 3 and 4 show an example of neuroplasticity in which the brain compensates for a loss of neural function in one region of the brain by recruiting other regions of the brain to perform neural activity for carrying out the affected neural function. The diagnostic procedure 102 utilizes the neuroplasticity that occurs in the brain to identify the location of a stimulation site that is expected to be more responsive to the results of an electrical, magnetic, sonic, genetic, biologic, and/or pharmaceutical procedure to effectuate the desired neural function.

One embodiment of the diagnostic procedure 102 involves generating the intended neural activity remotely from the first region 210 of the brain, and then detecting or sensing the location in the brain where the intended neural activity has been generated. The intended neural activity can be generated by applying an input that causes a signal to be sent to the brain. For example, in the case of a patient that has lost the use of a limb, the affected limb is moved and/or stimulated while the brain is scanned using a known imaging technique that can detect neural activity (e.g., functional MRI, positron emission tomography, etc.). In one specific embodiment, the affected limb can be moved by a practitioner or the patient, stimulated by sensory tests (e.g., pricking), or subject to peripheral electrical stimulation. The movement/stimulation of the affected limb produces a peripheral neural signal from the limb' that is expected to generate a response neural activity in the brain. The location in the brain where this response neural activity is present can be identified using the imaging technique. FIG. 4, for example, can be created by moving the affected fingers and then noting where neural activity occurs in response to the peripheral stimulus. By peripherally generating the intended neural activity, this embodiment may accurately identify where the brain has recruited matter (i.e., sites 220 and 230) to perform the intended neural activity associated with the neural function.

An alternative embodiment of the diagnostic procedure 102 involves identifying a stimulation site at a second location of the brain where the neural activity has changed in response to a change in the neural function of the patient. This embodiment of the method does not necessarily require that the intended neural activity be generated by peripherally actuating or stimulating a body part. For example, the brain can be scanned for neural activity associated with the impaired neural function as a patient regains use of an affected limb or learns a task over a period of time. This embodiment, however, can also include peripherally generating the intended neural activity remotely from the brain explained above.

In still another embodiment, the diagnostic procedure 102 involves identifying a stimulation site at a location of the brain where the intended neural activity is developing to perform the neural function. This embodiment is similar to the other embodiments of the diagnostic procedure 102, but it can be used to identify a stimulation site at (a) the normal region of the brain where the intended neural activity is expected to occur according to the functional organization of the brain and/or (b) a different region where the neural activity occurs because the brain is recruiting additional matter to perform the neural function. This particular embodiment of the method involves monitoring neural activity at one or more locations where the neural activity occurs in response to the particular neural function of interest. For example, to enhance the ability to learn a particular task (e.g., playing a musical instrument, memorizing, etc.), the neural activity can be monitored while a person performs the task or thinks about performing the task. The stimulation sites can be defined by the areas of the brain where the neural activity has the highest intensity, the greatest increases, and/or other parameters that indicate areas of the brain that are being used to perform the particular task.

FIGS. 5A and 5B are schematic illustrations of the implanting procedure 104 described above with reference to FIG. 1C for positioning the first and second electrodes relative to a portion of the brain of a patient 500. Referring to FIG. 5A, a stimulation site 502 is identified in accordance with an embodiment of the diagnostic procedure 102. In one embodiment, a skull section 504 is removed from the patient 500 adjacent to the stimulation site 502. The skull section 504 can be removed by boring a hole in the skull in a manner known in the art, or a much smaller hole can be formed in the skull using drilling techniques that are also known in the art. In general, the hole can be 0.2-4.0 cm in diameter. Referring to FIG. 5B, an implantable stimulation apparatus 510 having first and second electrodes 520 can be implanted in the patient 500. Suitable techniques associated with the implantation procedure are known to practitioners skilled in the art. After the stimulation apparatus 510 has been implanted in the patient 500, a pulse system generates electrical pulses that are transmitted to the stimulation site 502 by the first and second electrodes 520. Stimulation apparatus suitable for carrying out the foregoing embodiments of methods in accordance with the invention are described in more detail below with reference to the FIGS. 6-40.

Several embodiments of methods for enhancing neural activity in accordance with the invention are expected to provide lasting results that promote the desired neural function. Before the present invention, electrical and magnetic stimulation techniques typically stimulated the normal locations of the brain where neural activity related to the neural functions occurred according to the functional organization of the brain. Such conventional techniques, however, may not be effective because the neurons in the "normal locations" of the brain may not be capable of carrying out the neural activity because of brain damage, disease, disorder, and/or because of variations of the location specific to individual patients. Several embodiments of methods for enhancing neural activity in accordance with the invention overcome this drawback by identifying a stimulation site based on neuroplastic activity that appears to be related to the neural function. By first identifying a location in the brain that is being recruited to perform the neural activity, it is expected that therapies (e.g., electrical, magnetic, genetic, biologic, and/or pharmaceutical) applied to this location will be more effective than conventional techniques. This is because the location that the brain is recruiting for the neural activity may not be the "normal location" where the neuro activity would normally occur according to the functional organization of the brain. Therefore, several embodiments of methods for enhancing neural activity in accordance with the invention are expected to provide lasting results because the therapies are applied to the portion of the brain where neural activity for carrying out the neural function actually occurs in the particular patient.

2. Electrically Inducing Desired Neural Activity

The method 100 for effectuating a neural function can also be used to induce neural activity in a region of the brain where such neural activity is not present. As opposed to the embodiments of the method 100 described above for enhancing existing neural activity, the embodiments of the method 100 for inducing neural activity initiate the neural activity at a stimulation site where it is estimated that neuroplasticity will occur. In this particular situation, an image of the brain seeking to locate where neuroplasticity is occurring may be similar to FIG. 3. An aspect of inducing neural activity, therefore, is to develop a procedure to determine where neuroplasticity is likely to occur.

A stimulation site may be identified by estimating where the brain will likely recruit neurons for performing the neural function. In one embodiment, the location of the stimulation site is estimated by defining a region of the brain that is proximate to the normal location where neural activity related to the neural function is generally present according to the functional organization of the brain. An alternative embodiment for locating the stimulation site includes determining where neuroplasticity has typically occurred in patients with similar symptoms. For example, if the brain typically recruits a second region of the cortex to compensate for a loss of neural activity in the normal region of the cortex, then the second region of the cortex can be selected as the stimulation site either with or without imaging the neural activity in the brain.

Several embodiments of methods for inducing neural activity in accordance with the invention are also expected to provide lasting results that initiate and promote a desired neural function. By first estimating the location of a stimulation site where desired neuroplasticity is expected to occur, therapies applied to this location may be more effective than conventional therapies for reasons that are similar to those explained above regarding enhancing neural activity. Additionally, methods for inducing neural activity may be easier and less expensive to implement because they do not require generating neural activity and/or imaging the brain to determine where the intended neural activity is occurring before applying the therapy.

3. Applications of Methods for Electrically Stimulating Regions of the Brain

The foregoing methods for enhancing existing neural activity or inducing new neural activity are expected to be useful for many applications. As explained above, several embodiments of the method 100 involve determining an efficacious location of the brain to enhance or induce an intended neural activity that causes the desired neural functions to occur. Additional therapies can also be implemented in combination with the electrical stimulation methods described above. Several specific applications using embodiments of electrical stimulation methods in accordance with the invention either alone or with adjunctive therapies will now be described, but it will be appreciated that the methods in accordance with the invention can be used in many additional applications.

a. General Applications

The embodiments of the electrical stimulation methods described above are expected to be particularly useful for rehabilitating a loss of mental functions, motor functions and/or sensory functions caused by damage to the brain. In a typical application, the brain has been damaged by a stroke or trauma (e.g., automobile accident). The extent of the particular brain damage can be assessed using functional MRI or another appropriate imaging technique as explained above with respect to FIG. 3. A stimulation site can then be identified by: (a) peripherally stimulating a body part that was affected by the brain damage to induce the intended neural activity and determining the location where a response neural activity occurs; (b) determining where the neural activity has changed as a patient gains more use of the affected body part; and/or (c) estimating the location that the brain may recruit neurons to carry out the neural activity that was previously performed by the damaged portion of the brain. An electrical stimulation therapy can then be applied to the selected stimulation site by placing the first and second electrodes relative to the stimulation site to apply an electrical current in that portion of the brain. As explained in more detail below, it is expected that applying an electrical current to the portion of the brain that has been recruited to perform the neural activity related to the affected body part will produce a lasting neurological effect for rehabilitating the affected body part.

Several specific applications are expected to have a stimulation site in the cortex because neural activity in this part of the brain effectuates motor functions and/or sensory functions that are typically affected by a stroke or trauma. In these applications, the electrical stimulation can be applied directly to the pial surface of the brain or at least proximate to the pial surface (e.g., the dura mater, the fluid surrounding the cortex, or neurons within the cortex). Suitable devices for applying the electrical stimulation to the cortex are described in detail with reference to FIGS. 6-40.

The electrical stimulation methods can also be used with adjunctive therapies to rehabilitate damaged portions of the brain. In one embodiment, the electrical stimulation methods can be combined with physical therapy and/or drug therapies to rehabilitate an affected neural function. For example, if a stroke patient has lost the use of a limb, the patient can be treated by applying the electrical therapy to a stimulation site where the intended neural activity is present while the affected limb is also subject to physical therapy. An alternative embodiment can involve applying the electrical therapy to the stimulation site and chemically treating the patient using amphetamines or other suitable drugs.

The embodiments of the electrical stimulation methods described above are also expected to be useful for treating brain diseases, such as Alzheimer's, Parkinson's, and other brain diseases. In this application, the stimulation site can be identified by monitoring the neural activity using functional MRI or other suitable imaging techniques over a period of time to determine where the brain is recruiting material to perform the neural activity that is being affected by the disease. It may also be possible to identify the stimulation site by having the patient try to perform an act that the particular disease has affected, and monitoring the brain to determine whether any response neural activity is present in the brain. After identifying where the brain is recruiting additional matter, the electrical stimulation can be applied to this portion of the brain. It is expected that electrically stimulating the regions of the brain that have been recruited to perform the neural activity which was affected by the disease will assist the brain in offsetting the damage caused by the disease.

The embodiments of the electrical stimulation methods described above are also expected to be useful for treating neurological disorders, such as depression, passive-aggressive behavior, weight control, and other disorders. In these applications, the electrical stimulation can be applied to a stimulation site in the cortex or another suitable part of the brain where neural activity related to the particular disorder is present. The embodiments of electrical stimulation methods for carrying out the particular therapy can be adapted to either increase or decrease the particular neural activity in a manner that produces the desired results. For example, an amputee may feel phantom sensations associated with the amputated limb. This phenomenon can be treated by applying an electrical pulse that reduces the phantom sensations. The electrical therapy can be applied so that it will modulate the ability of the neurons in that portion of the brain to execute sensory functions.

b. Pulse Forms and Potentials

The electrical stimulation methods in accordance with the invention can use several different pulse forms to effectuate the desired neuroplasticity. The pulses can be a bi-phasic or monophasic stimulus that is applied to achieve a desired potential in a sufficient percentage of a population of neurons at the stimulation site. In one embodiment, the pulse form has a frequency of approximately 2-1000 Hz, but the frequency may be particularly useful in the range of approximately 40-200 Hz. For example, initial clinical trials are expected to use a frequency of approximately 50-100 Hz. The pulses can also have pulse widths of approximately 10 µs-100 ms, or more specifically the pulse width can be approximately 20-200 µs. For example, a pulse width of 50-100 µs may produce beneficial results.

One possible application of the invention involves enhancing or inducing neuroplasticity by raising the resting membrane potential of neurons to bring the neurons closer to the threshold level for firing an action potential. This model is based on the premise that the resting potential of the membrane can change. Because the stimulation raises the resting membrane potential of the neurons, it is expected that these neurons are more likely to "fire" an action potential in response to excitatory input at a lower level. Another model for enhancing or inducing neural plasticity is based on the premise that EEN stimulation generates a widespread nonselective activation of many synaptic connections throughout the cortex. This neural activity depolarizes the postsynaptic membrane and may momentarily remove the magnesium ion from NMDA channels. If a synapse is then activated by behaviorally induced activity before the magnesium block is re-established, calcium ions can more easily flow into the cell and trigger LTP. EEN induced removal of the magnesium block would briefly enhance the neuron's susceptibility for LTP. Subsequent behavioral activation of the synaptic connection would then trigger LTP and strengthen the connection. In either model, the electrical stimulation enhances or induces neural plasticity to carry out an intended neural function.

FIG. 5C is a graph illustrating applying a subthreshold potential to the neurons N1-N3 of FIG. 1A. At times $t_1$ and $t_2$, the excitory/inhibitory inputs from other neurons do not "bridge-the-gap" from the resting potential at −X mV to the threshold potential. At time $t_3$, the electrical stimulation is applied to the brain to raise the resting potential of neurons in the stimulated population such that the resting potential is at −Y mV. As such, at time $t_4$ when the neurons receive another excitatory input, even a small input exceeds the gap between the raised resting potential −Y mV and the threshold potential to induce action potentials in these neurons. For example, if the resting potential is approximately −70 mV and the threshold potential is approximately −50 mV, then the electrical stimulation can be applied to raise the resting potential of a sufficient number of neurons to approximately −52 to −60 mV.

The actual electrical potential applied to electrodes implanted in the brain to achieve a subthreshold potential stimulation will vary according to the individual patient, the type of therapy, the type of electrodes, and other factors. In general, the pulse form of the electrical stimulation (e.g., the frequency, pulse width, wave form, and voltage potential) is selected to raise the resting potential in a sufficient number of neurons at the stimulation site to a level that is less than a threshold potential for a statistical portion of the neurons in the population. The pulse form, for example, can be selected so that the applied voltage of the stimulus achieves a change in the resting potential of approximately 10%-95%, and more specifically of 60%-80%, of the difference between the unstimulated resting potential and the threshold potential.

In one specific example of a subthreshold application for treating a patient's hand, electrical stimulation is not initially applied to the stimulation site. Although physical therapy related to the patient's hand may cause some activation of a particular population of neurons that is known to be involved in "hand function," only a low level of activation might occur because physical therapy only produces a low level of action potential generation in that population of neurons. However, when the subthreshold electrical stimulation is applied, the resting membrane potentials of the neurons in the stimulated population are elevated. These neurons now are much closer to the threshold for action potential formation such that when the same type of physical therapy is given, this population of cells will have a higher level of activation because these cells are more likely to fire action potentials.

Subthreshold stimulation may produce better results than simply stimulating the neurons with sufficient energy levels to exceed the threshold for action potential formation. One aspect of subthreshold stimulation is to increase the probability that action potentials will occur in response to the ordinary causes of activation—such as physical therapy. This will allow the neurons in this functional network to become entrained together, or "learn" to become associated with these types of activities. If neurons are given so much electricity that they continually fire action potentials without additional excitatory inputs (suprathreshold stimulation), this will create "noise" and disorganization that will not likely cause improvement in function. In fact, neurons that are "over-driven" soon deplete their neurotransmitters and effectively become silent.

The application of a subthreshold stimulation is very different than suprathreshold stimulation. Subthreshold stimulation in accordance with several embodiments of the invention, for example, does not intend to directly make neurons fire action potentials with the electrical stimulation in a significant population of neurons at the stimulation site. Instead, subthreshold stimulation attempts to decrease the "activation energy" required to activate a large portion of the neurons at the stimulation site. As such, subthreshold stimulation in accordance with certain embodiments of the invention is expected to increase the probability that the neurons will fire in response to the usual intrinsic triggers, such as trying to move a limb, physical therapy, or simply thinking about movement of a limb, etc. Moreover, coincident stimulation associated with physical therapy is expected to increase the probability that the action potentials that are occurring with an increased probability due to the subthreshold stimulation will be related to meaningful triggers, and not just "noise."

The stimulus parameters set forth above, such as a frequency selection of approximately 50-100 Hz and an amplitude sufficient to achieve an increase of 60% to 80% of the difference between the resting potential and the threshold potential are specifically selected so that they will increase the resting membrane potential of the neurons, thereby increasing the likelihood that they will fire action potentials, without directly causing action potentials in most of the neuron population. In addition, and as explained in more detail below with respect to FIGS. 6-40, several embodiments of stimulation apparatus in accordance with the invention are designed to precisely apply a pulse form that produces subthreshold stimulation by selectively stimulating regions of the cerebral cortex of approximately 1-2 cm (the estimated size of a "functional unit" of cortex), directly contacting the pial surface with the electrodes to consistently create the same alterations in resting membrane potential, and/or biasing the electrodes against the pial surface to provide a positive connection between the electrodes and the cortex.

B. Devices for Electrically Stimulating Regions of the Brain

FIGS. 6-40 illustrate stimulation apparatus in accordance with several embodiments of the invention for electrically stimulating regions of the brain in accordance with one or more of the methods described above. The devices illustrated in FIGS. 6-40 are generally used to stimulate a region of the cortex proximate to the pial surface of the brain (e.g., the dura mater, the pia mater, the fluid between the dura mater and the pia mater, and a depth in the cortex outside of the white matter of the brain). The devices can also be adapted for stimulating other portions of the brain in other embodiments.

1. Implantable Stimulation Apparatus with Integrated Pulse Systems

Figure 6:
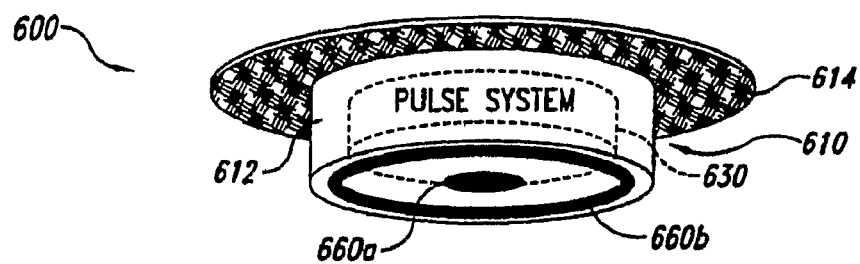
FIG. 6 is an isometric view of an implantable stimulation apparatus in accordance with one embodiment of the invention.
Figure 7:
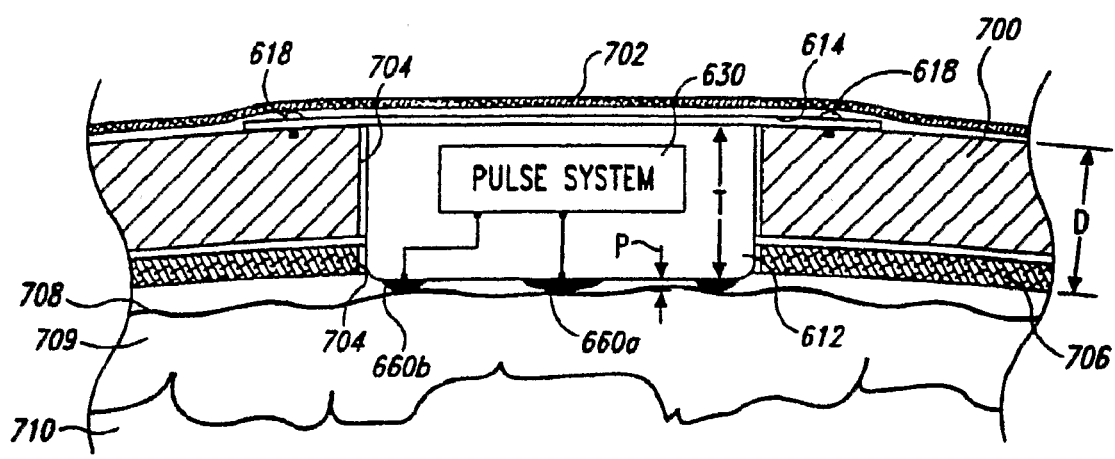
FIG. 7 is a cross-sectional view schematically illustrating a part of an implantable stimulation apparatus in accordance with an embodiment of the invention.

FIG. 6 is an isometric view and FIG. 7 is a cross-sectional view of a stimulation apparatus 600 in accordance with an embodiment of the invention for stimulating a region of the cortex proximate to the pial surface. In one embodiment, the stimulation apparatus 600 includes a support member 610, an integrated pulse-system 630 (shown schematically) carried by the support member 610, and first and second electrodes 660 (identified individually by reference numbers 660a and 660b). The first and second electrodes 660 are electrically coupled to the pulse system 630. The support member 610 can be configured to be implanted into the skull or another intracranial region of a patient. In one embodiment, for example, the support member 610 includes a housing 612 and an attachment element 614 connected to the housing 612. The housing 612 can be a molded casing formed from a biocompatible material that has an interior cavity for carrying the pulse system 630. The housing can alternatively be a biocompatible metal or another suitable material. The housing 612 can have a diameter of approximately 1-4 cm, and in many applications the housing 612 can be 1.5-2.5 cm in diameter. The housing 612 can also have other shapes (e.g., rectilinear, oval, elliptical) and other surface dimensions. The stimulation apparatus 600 can weigh 35 g or less and/or occupy a volume of 20 cc or less. The attachment element 614 can be a flexible cover, a rigid plate, a contoured cap, or another suitable element for holding the support member 610 relative to the skull or other body part of the patient. In one embodiment, the attachment element 614 is a mesh, such as a biocompatible polymeric mesh, metal mesh, or other suitable woven material. The attachment element 614 can alternatively be a flexible sheet of Mylar, a polyester, or another suitable material.

FIG. 7, more specifically, is a cross-sectional view of the stimulation apparatus 600 after it has been implanted into a patient in accordance with an embodiment of the invention. In this particular embodiment, the stimulation apparatus 600 is implanted into the patient by forming an opening in the scalp 702 and cutting a hole 704 through the skull 700 and through the dura mater 706. The hole 704 should be sized to receive the housing 612 of the support member 610, and in most applications, the hole 704 should be smaller than the attachment element 614. A practitioner inserts the support member 610 into the hole 704 and then secures the attachment element 614 to the skull 700. The attachment element 614 can be secured to the skull using a plurality of fasteners 618 (e.g., screws, spikes, etc.) or an adhesive. In an alternative embodiment, a plurality of downwardly depending spikes can be formed integrally with the attachment element 614 to define anchors that can be driven into the skull 700.

The embodiment of the stimulation apparatus 600 shown in FIG. 7 is configured to be implanted into a patient so that the electrodes 660 contact a desired portion of the brain at the stimulation site. The housing 612 and the electrodes 660 can project from the attachment element 614 by a distance "D" such that the electrodes 660 are positioned at least proximate to the pia mater 708 surrounding the cortex 709. The electrodes 660 can project from a housing 612 as shown in FIG. 7, or the electrodes 660 can be flush with the interior surface of the housing 612. In the particular embodiment shown in FIG. 7, the housing 612 has a thickness "T" and the electrodes 660 project from the housing 612 by a distance "P" so that the electrodes 660 press against the surface of the pia mater 708. The thickness of the housing 612 can be approximately 0.5-4 cm, and is more generally about 1-2 cm. The configuration of the stimulation apparatus 600 is not limited to the embodiment shown in FIGS. 6 and 7, but rather the housing 612, the attachment element 614, and the electrodes 660 can be configured to position the electrodes in several different regions of the brain. For example, in an alternate embodiment, the housing 612 and the electrodes 660 can be configured to position the electrodes deep within the cortex 709, and/or a deep brain region 710. In general, the electrodes can be flush with the housing or extend 0.1 mm to 5 cm from the housing. More specific embodiments of pulse system and electrode configurations for the stimulation apparatus will be described below.

Several embodiments of the stimulation apparatus 600 are expected to be more effective than existing transcranial electrical stimulation devices and transcranial magnetic stimulation devices. It will be appreciated that much of the power required for transcranial therapies is dissipated in the scalp and skull before it reaches the brain. In contrast to conventional transcranial stimulation devices, the stimulation apparatus 600 is implanted so that the electrodes are at least proximate to the pial surface of the brain 708. Several embodiments of methods in accordance with the invention can use the stimulation apparatus 600 to apply an electrical therapy directly to the pia mater 708, the dura mater 706, and/or another portion of the cortex 709 at significantly lower power levels than existing transcranial therapies. For example, a potential of approximately 1 mV to 10 V can be applied to the electrodes 660; in many instances a potential of 100 mV to 5 V can be applied to the electrodes 660 for selected applications. It will also be appreciated that other potentials can be applied to the electrodes 660 of the stimulation apparatus 600 in accordance with other embodiments of the invention.

Selected embodiments of the stimulation apparatus 600 are also capable of applying stimulation to a precise stimulation site. Again, because the stimulation apparatus 600 positions the electrodes 660 at least proximate to the pial surface 708, precise levels of stimulation with good pulse shape fidelity will be accurately transmitted to the stimulation site in the brain. It will be appreciated that transcranial therapies may not be able to apply stimulation to a precise stimulation site because the magnetic and electrical properties of the scalp and skull may vary from one patient to another such that an identical stimulation by the transcranial device may produce a different level of stimulation at the neurons in each patient. Moreover, the ability to focus the stimulation to a precise area is hindered by delivering the stimulation transcranially because the scalp, skull and dura all diffuse the energy from a transcranial device. Several embodiments of the stimulation apparatus 600 overcome this drawback because the electrodes 660 are positioned under the skull 700 such that the pulses generated by the stimulation apparatus 600 are not diffused by the scalp 702 and skull 700.

2. Integrated Pulse Systems for Implantable Stimulation Apparatus

The pulse system 630 shown in FIGS. 6 and 7 generates and/or transmits electrical pulses to the electrodes 660 to create an electrical field at a stimulation site in a region of the brain. The particular embodiment of the pulse system 630 shown in FIG. 7 is an "integrated" unit in that is carried by the support member 610. The pulse system 630, for example, can be housed within the housing 612 so that the electrodes 660 can be connected directly to the pulse system 630 without having leads outside of the stimulation apparatus 600. The distance between the electrodes 660 and the pulse system 630 can be less than 4 cm, and it is generally 0.10 to 2.0 cm. The stimulation apparatus 600 can accordingly provide electrical pulses to the stimulation site without having to surgically create tunnels running through the patient to connect the electrodes 660 to a pulse generator implanted remotely from the stimulation apparatus 600. It will be appreciated, however, that alternative embodiments of stimulation apparatus in accordance with the invention can include a pulse system implanted separately from the stimulation apparatus 600 in the cranium or an external pulse system. Several particular embodiments of pulse systems that are suitable for use with the stimulation apparatus 600 will now be described in more detail.

Figure 8:
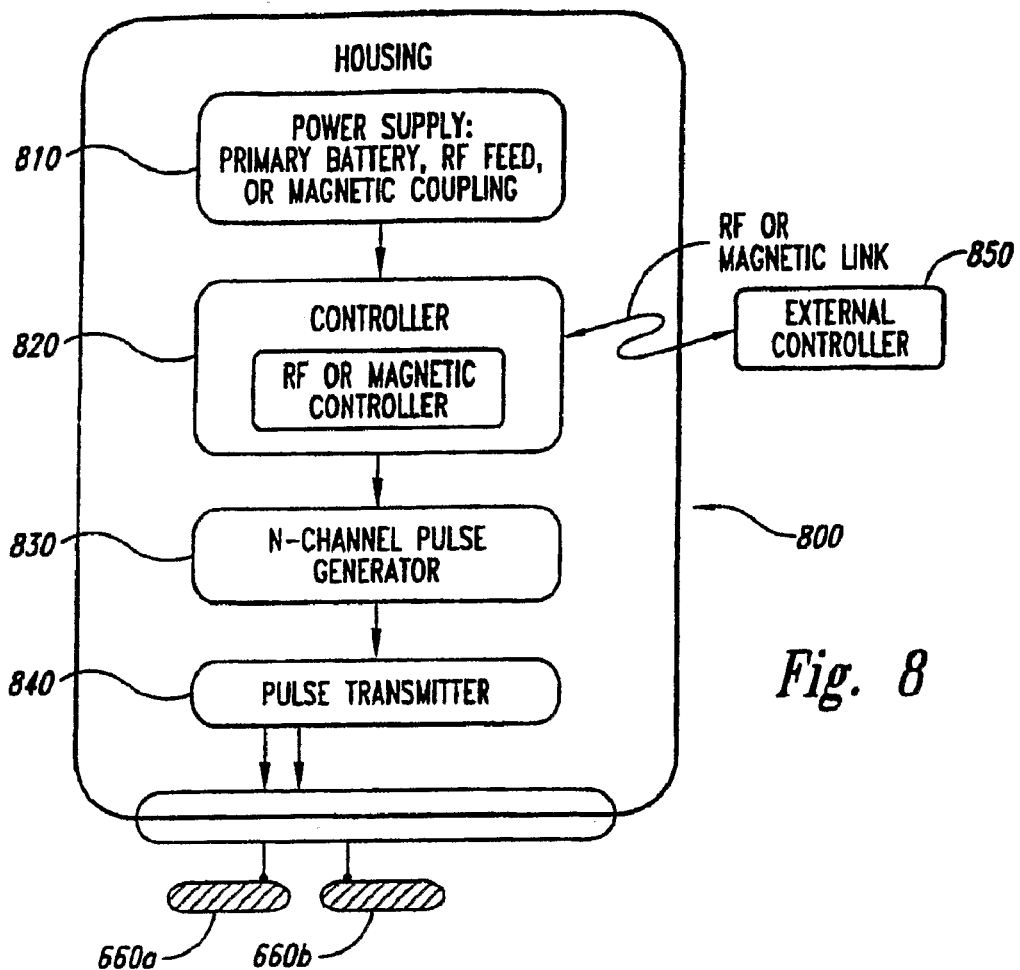
FIG. 8 is a schematic illustration of a pulse system in accordance with one embodiment of the invention.
Figure 9:
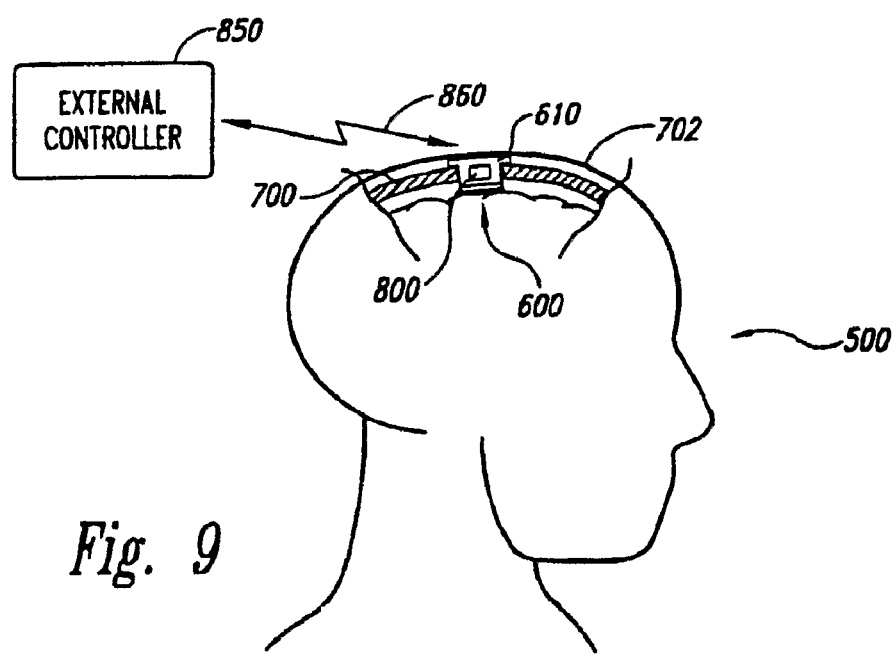
FIG. 9 is a schematic illustration of an implanted stimulation apparatus and an external controller in accordance with an embodiment of the invention.

FIGS. 8 and 9 schematically illustrate an integrated pulse system 800 in accordance with one embodiment of the invention for being implanted in the cranium within the stimulation apparatus 600. Referring to FIG. 8, the pulse system 800 can include a power supply 810, an integrated controller 820, a pulse generator 830, and a pulse transmitter 840. The power supply 810 can be a primary battery, such as a rechargeable battery or another suitable device for storing electrical energy. In alternative embodiments, the power supply 810 can be an RF transducer or a magnetic transducer that receives broadcast energy emitted from an external power source and converts the broadcast energy into power for the electrical components of the pulse system 800. The integrated controller 820 can be a wireless device that responds to command signals sent by an external controller 850. The integrated controller 820, for example, can communicate with the external controller 850 by RF or magnetic links 860. The integrated controller 820 provides control signals to the pulse generator 830 in response to the command signals sent by the external controller 850. The pulse generator 830 can have a plurality of channels that send appropriate electrical pulses to the pulse transmitter 840, which is coupled to the electrodes 660. Suitable components for the power supply 810, the integrated controller 820, the pulse generator 830, and the pulse transmitter 840 are known to persons skilled in the art of implantable medical devices.

Referring to FIG. 9, the pulse system 800 can be carried by the support member 610 of the stimulation apparatus 600 in the manner described above with reference to FIGS. 6 and 7. The external controller 850 can be located externally to the patient 500 so that the external controller 850 can be used to control the pulse system 800. In one embodiment, several patients that require a common treatment can be simultaneously treated using a single external controller 850 by positioning the patients within the operating proximity of the controller 850. In an alternative embodiment, the external controller 850 can contain a plurality of operating codes and the integrated controller 820 for a particular patient can have an individual operating code. A single controller 850 can thus be used to treat a plurality of different patients by entering the appropriate operating code into the controller 850 corresponding to the particular operating codes of the integrated controllers 820 for the patients.

Figure 10:
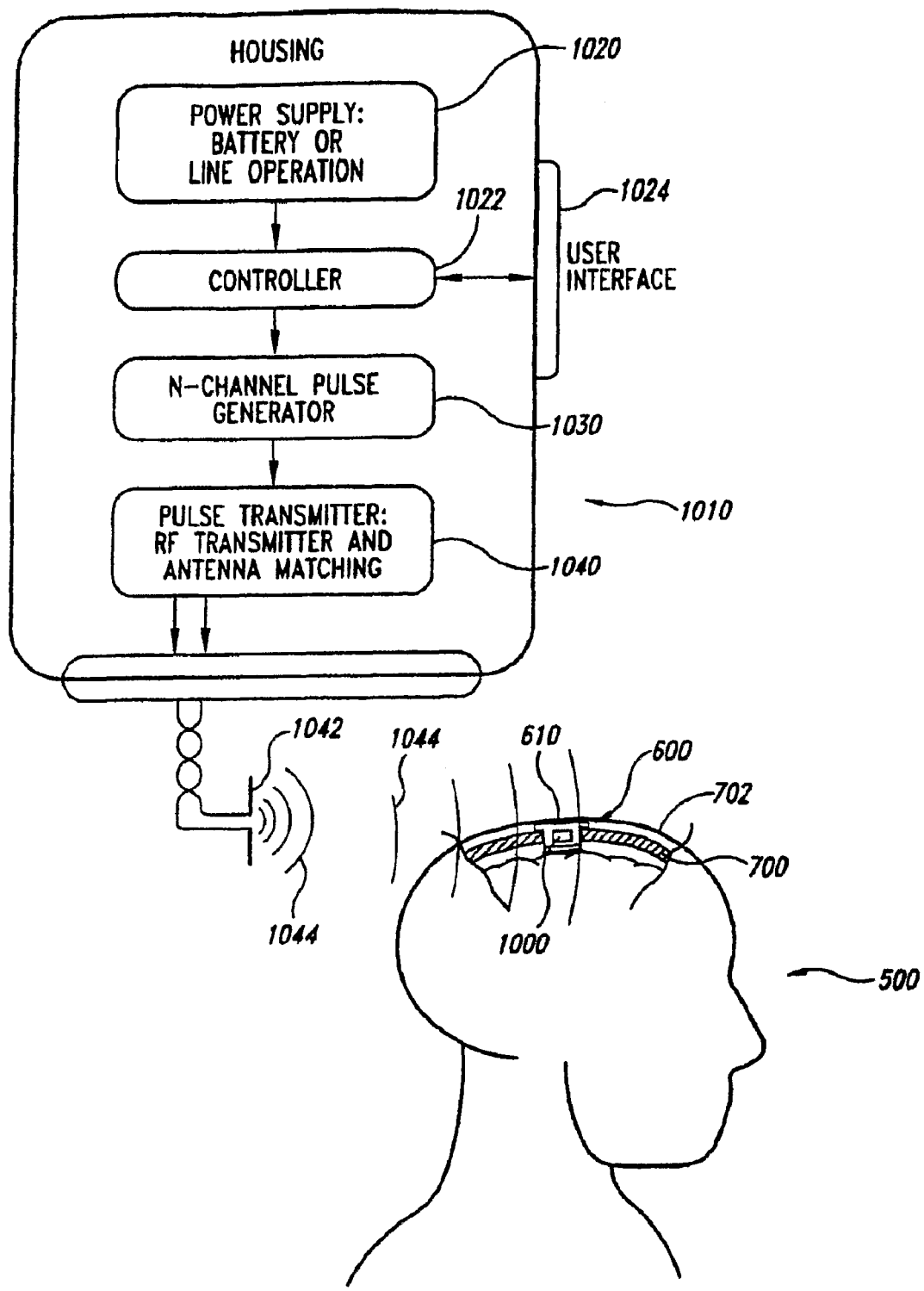
FIG. 10 is a schematic illustration of an implantable stimulation apparatus having a pulse system and an external controller in accordance with another embodiment of the invention.

FIG. 10 is a schematic view illustrating a pulse system 1000 and an external controller 1010 for use with the stimulation apparatus 600 in accordance with another embodiment of the invention. In this embodiment, the external controller 1010 includes a power supply 1020, a controller 1022 coupled to the power supply 1020, and a user interface 1024 coupled to the controller 1022. The external controller 1010 can also include a pulse generator 1030 coupled to the power supply 1020, a pulse transmitter 1040 coupled to the pulse generator 1030, and an antenna 1042 coupled to the pulse transmitter 1040. The external controller 1010 generates the power and the pulse signal, and the antenna 1042 transmits a pulse signal 1044 to the pulse system 1000 in the stimulation apparatus 600. The pulse system 1000 receives the pulse signal 1044 and delivers an electrical pulse to the electrodes. The pulse system 1000, therefore, does not necessarily include an integrated power supply, controller and pulse generator within the housing 610 because these components are in the external controller 1010.

Figure 11:
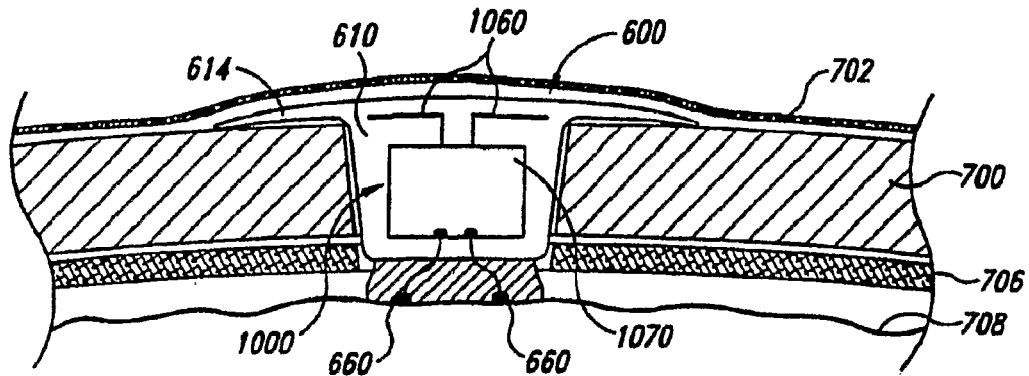
FIG. 11 is a cross-sectional view schematically illustrating a part of an implantable stimulation apparatus in accordance with an embodiment of the invention.

FIG. 11 is a schematic view illustrating an embodiment of the pulse system 1000 in greater detail. In this embodiment, the pulse system 1000 is carried by the support member 610 of the stimulation apparatus 600. The pulse system 1000 can include an antenna 1060 and a pulse delivery system 1070 coupled to the antenna 1060. The antenna 1060 receives the pulse signal 1044 from the external controller 1010 and sends the pulse signal 1044 to the pulse delivery system 1070, which transforms the pulse signal 1044 into electrical pulses. Accordingly, the electrodes 660 can be coupled to the pulse delivery system 1070. The pulse delivery system 1070 can include a filter to remove noise from the pulse signal 1044 and a pulse former that creates an electrical pulse from the pulse signal 1044. The pulse former can be driven by the energy in the pulse signal 1044, or in an alternative embodiment, the pulse system 1000 can also include an integrated power supply to drive the pulse former.

Figure 12:
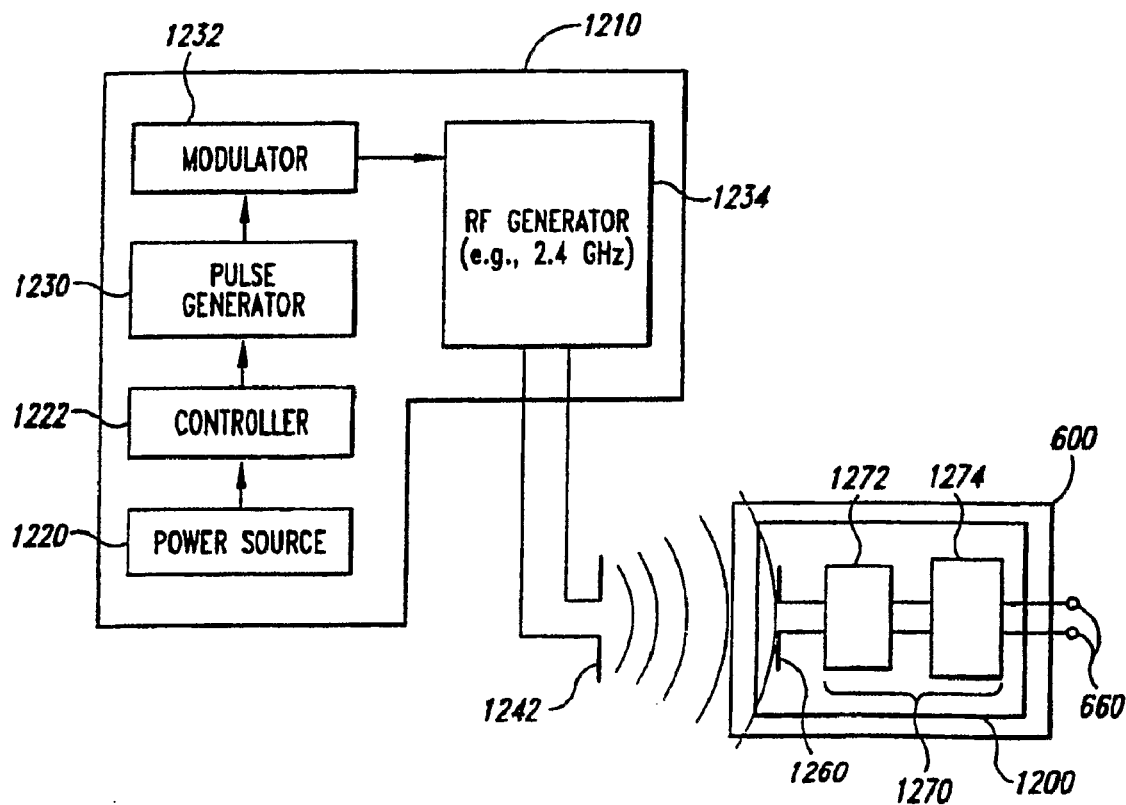
FIG. 12 is a schematic illustration of an implantable stimulation apparatus having a pulse system and an external controller in accordance with another embodiment of the invention.

FIG. 12 is a schematic view illustrating an embodiment of pulse system 1200 for use in an embodiment of the stimulation apparatus 600, and an external controller 1210 for controlling the pulse system 1200 remotely from the patient using RF energy. In this embodiment, the external controller 1210 includes a power supply 1220, a controller 1222 coupled to the power supply 1220, and a pulse generator 1230 coupled to the controller 1222. The external controller 1210 can also include a modulator 1232 coupled to the pulse generator 1230 and an RF generator 1234 coupled to the modulator 1232. In operation, the external controller 1210 broadcasts pulses of RF energy via an antenna 1242.

The pulse system 1200 can be housed within the stimulation apparatus 600 (not shown). In one embodiment, the pulse system 1200 includes an antenna 1260 and a pulse delivery system 1270. The antenna 1260 incorporates a diode (not shown) that rectifies the broadcast RF energy from the antenna 1242. The pulse delivery system 1270 can include a filter 1272 and a pulse former 1274 that forms electrical pulses which correspond to the RF energy broadcast from the antenna 1242. The pulse system 1200 is accordingly powered by the RF energy in the pulse signal from the external controller 1210 such that the pulse system 1200 does not need a separate power supply carried by the stimulation apparatus 600.

Figure 13:
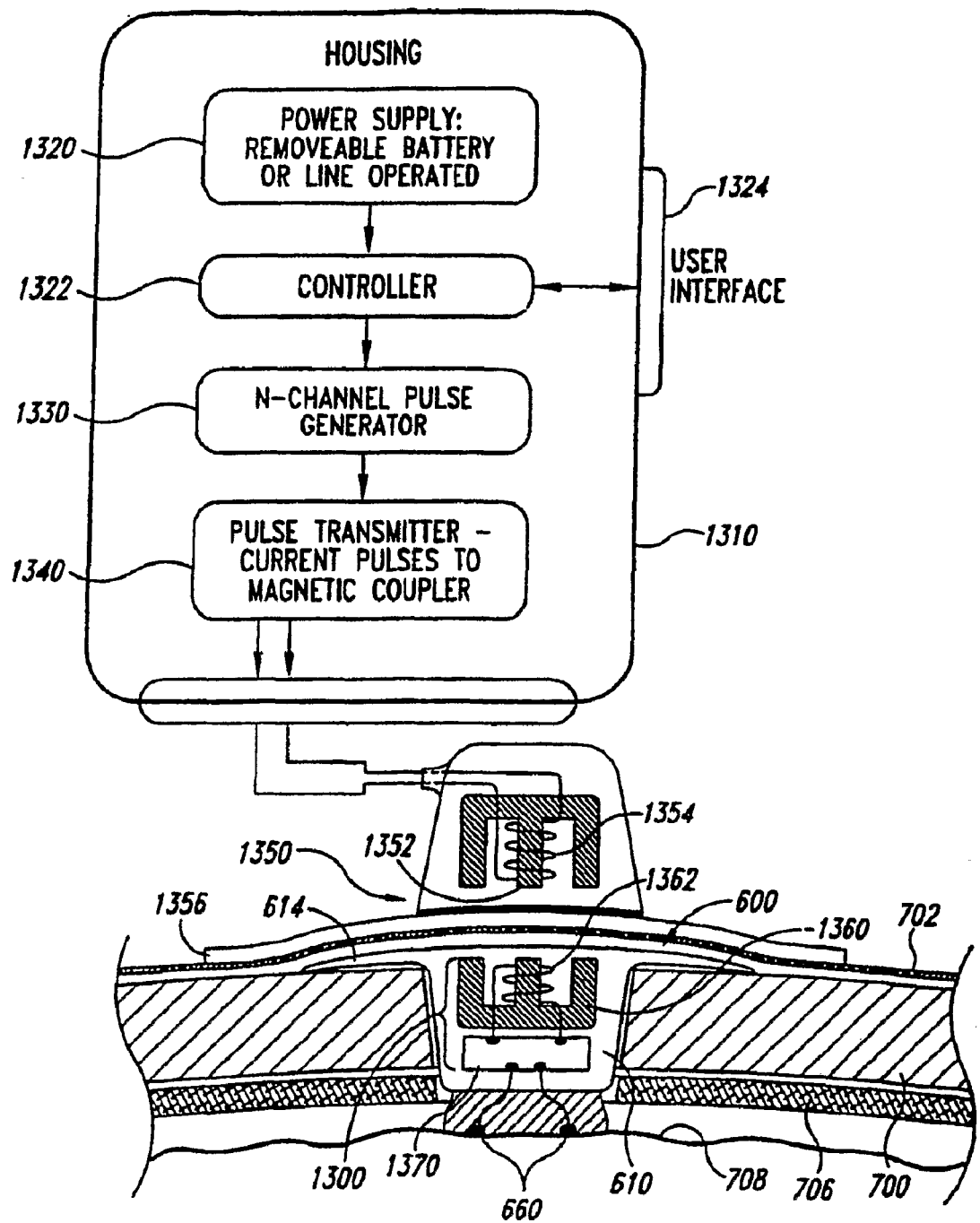
FIG. 13 is a cross-sectional view schematically illustrating a part of an implantable stimulation apparatus having a pulse system and an external controller in accordance with another embodiment of the invention.

FIG. 13 is a cross-sectional view of a pulse system 1300 for use in another embodiment of the implantable stimulation apparatus 600, together with an external controller 1310 for remotely controlling the pulse system 1300 externally from the patient using magnetic energy. In this embodiment, the external controller 1310 includes a power supply 1320, a controller 1322 coupled to the power supply 1320, and a user interface 1324 coupled to the controller 1322. The external controller 1310 can also include a pulse generator 1330 coupled to the controller 1332, a pulse transmitter 1340 coupled to the pulse generator 1330, and a magnetic coupler 1350 coupled to the pulse transmitter 1340. The magnetic coupler 1350 can include a ferrite core 1352 and a coil 1354 wrapped around a portion of the ferrite core 1352. The coil 1354 can also be electrically connected to the pulse transmitter 1340 so that electrical pulses applied to the coil 1354 generate changes in a corresponding magnetic field. The magnetic coupler 1350 can also include a flexible cap 1356 to position the magnetic coupler 1350 over the implanted stimulation apparatus 600.

The pulse system 1300 can include a ferrite core 1360 and a coil 1362 wrapped around a portion of the ferrite core 1360. The pulse system 1310 can also include a pulse delivery system 1370 including a rectifier and a pulse former. In operation, the ferrite core 1360 and the coil 1362 convert the changes in the magnetic field generated by the magnetic coupler 1350 into electrical pulses that are sent to the pulse delivery system 1370. The electrodes 660 are coupled to the pulse delivery system 1370 so that electrical pulses corresponding to the electrical pulses generated by the pulse generator 1330 in the external controller 1310 are delivered to the stimulation site on the patient.

3. Electrode Configurations

Figure 21:
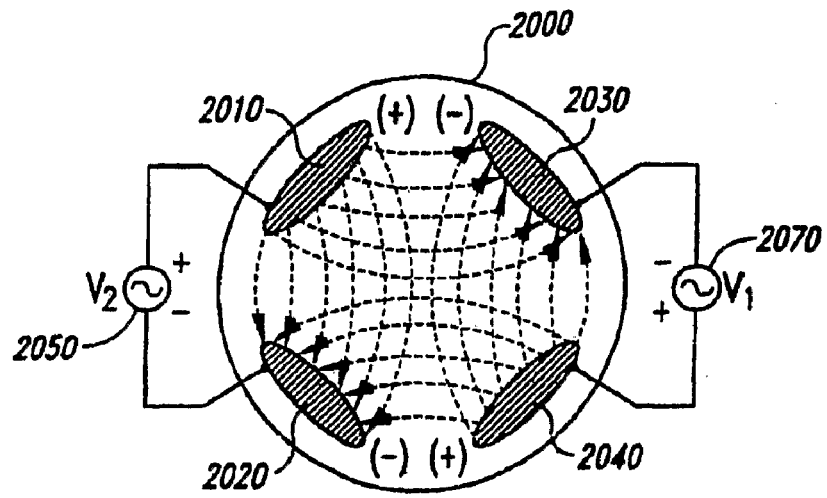
FIG. 21 is a bottom plan view of an electrode configuration for an implantable stimulation device in accordance with another embodiment of the invention.
Figure 22:
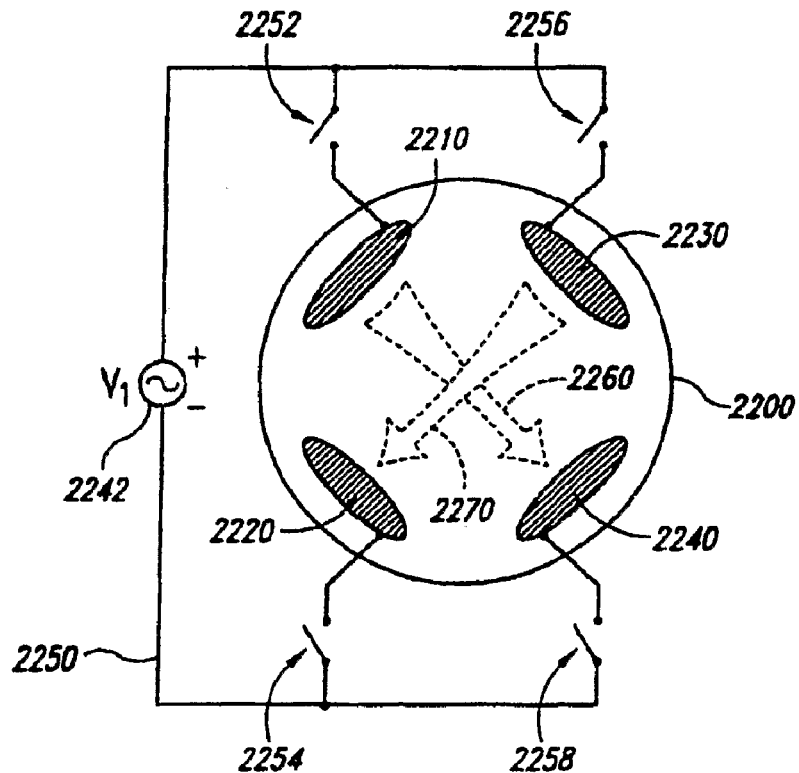
FIG. 22 is a bottom plan view of yet another embodiment of an electrode configuration for use with an implantable stimulation apparatus in accordance with the invention.
Figure 23:
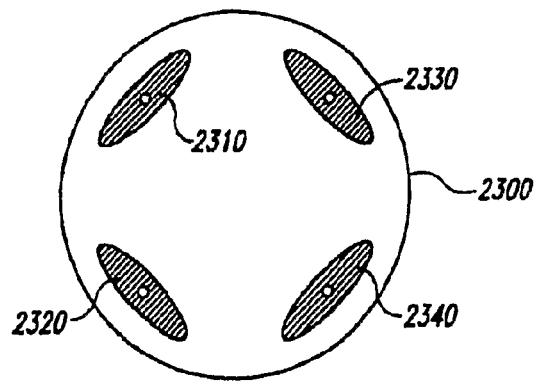
FIG. 23 is a bottom plan view.
Figure 24:
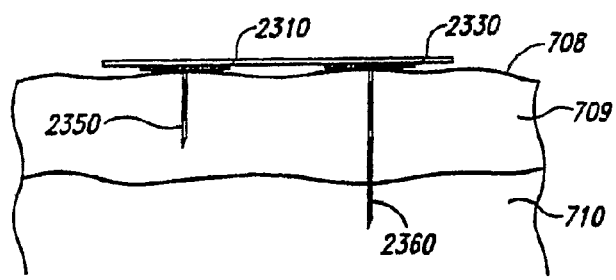
FIG. 24 is a cross-sectional view of an electrode configuration for use with a stimulation apparatus in accordance with still another embodiment of the invention.

FIGS. 14-24 illustrate electrodes in accordance with various embodiments of the invention that can be used with the stimulation apparatus disclosed herein. FIGS. 14-22 illustrate embodiments of electrodes configured to apply an electrical current to a stimulation site at least proximate to the pial surface of the cortex, and FIGS. 23 and 24 illustrate embodiments of electrodes configured to apply an electrical current within the cortex or below the cortex. It will be appreciated that other configurations of electrodes can also be used with other implantable stimulation apparatus.

Figure 14:
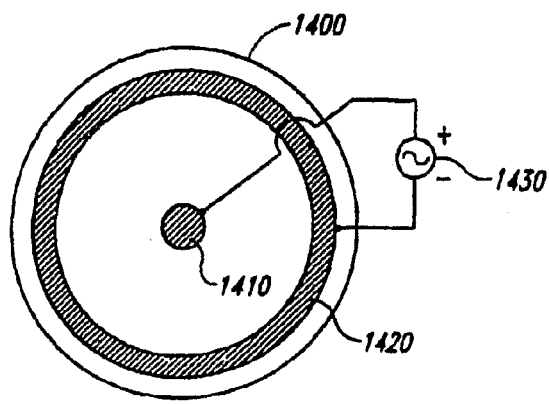
FIG. 14 is a bottom plan view.
Figure 15:
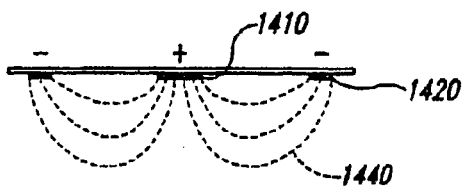
FIG. 15 is a cross-sectional view illustrating an electrode configuration for an implantable stimulation apparatus in accordance with an embodiment of the invention.

FIG. 14 is a bottom plan view and FIG. 15 is a cross-sectional view of a stimulation apparatus 1400 in accordance with an embodiment of the invention. In this embodiment, the stimulation apparatus 1400 includes a first electrode 1410 and a second electrode 1420 concentrically surrounding the first electrode 1410. The first electrode 1410 can be coupled to the positive terminal of a pulse generator 1430, and the second electrode 1420 can be coupled to the negative terminal of the pulse generator 1430. Referring to FIG. 15, the first and second electrodes 1410 and 1420 generate a toroidal electric field 1440.

Figure 16:
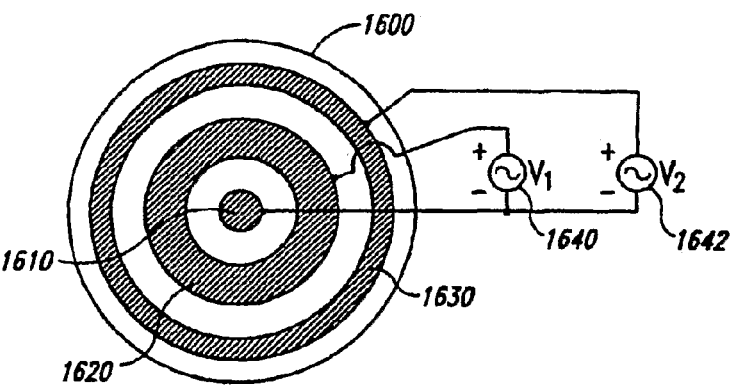
FIG. 16 is a bottom plan view.
Figure 17:
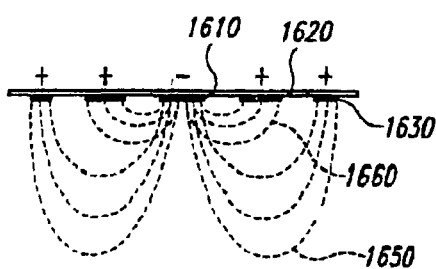
FIG. 17 is a cross-sectional view of an electrode configuration for an implantable stimulation apparatus in accordance with another embodiment of the invention.

FIG. 16 is a bottom plan view and FIG. 17 is a cross-sectional view of a stimulation apparatus 1600 in accordance with another embodiment of the invention. In this embodiment, the stimulation apparatus 1600 includes a first electrode 1610, a second electrode 1620 surrounding the first electrode 1610, and a third electrode 1630 surrounding the second electrode 1620. The first electrode 1610 can be coupled to the negative terminals of a first pulse generator 1640 and a second pulse generator 1642; the second electrode 1620 can be coupled to the positive terminal of the first pulse generator 1640; and the third electrode 1630 can be coupled to the positive terminal of the second pulse generator 1642. In operation, the first electrode 1610 and the third electrode 1630 generate a first toroidal electric field 1650, and the first electrode the 1610 and the second electrode 1620 generate a second toroidal electric field 1660. The second toroidal electric field 1660 can be manipulated to vary the depth that the first toroidal electric field 1650 projects away from the base of the stimulation apparatus 1600.

Figure 18:
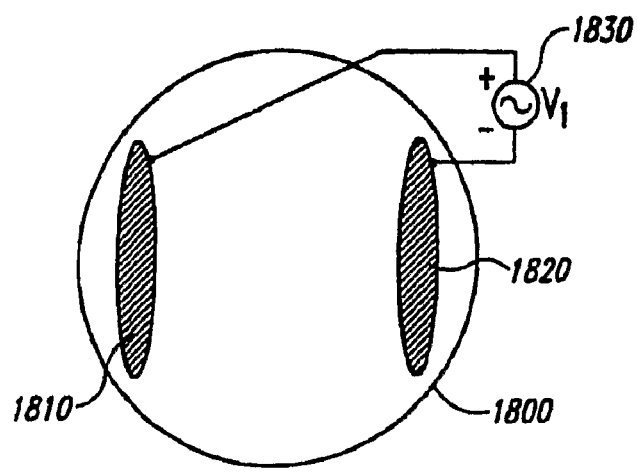
FIG. 18 is a bottom plan view.
Figure 19:
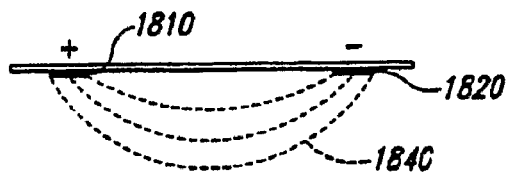
FIG. 19 is a cross-sectional view of an electrode configuration in accordance with yet another embodiment of the invention.

FIG. 18 is a bottom plan view and FIG. 19 is a cross-sectional view of a stimulation apparatus 1800 in accordance with yet another embodiment of the invention. In this embodiment, the stimulation apparatus 1800 includes a first electrode 1810 and a second electrode 1820 spaced apart from the first electrode 1810. The first and second electrodes 1810 and 1820 are linear electrodes which are coupled to opposite terminals of a pulse generator 1830. Referring to FIG. 19, the first and second electrodes 1810 and 1820 can generate an approximately linear electric field.

Figure 20:
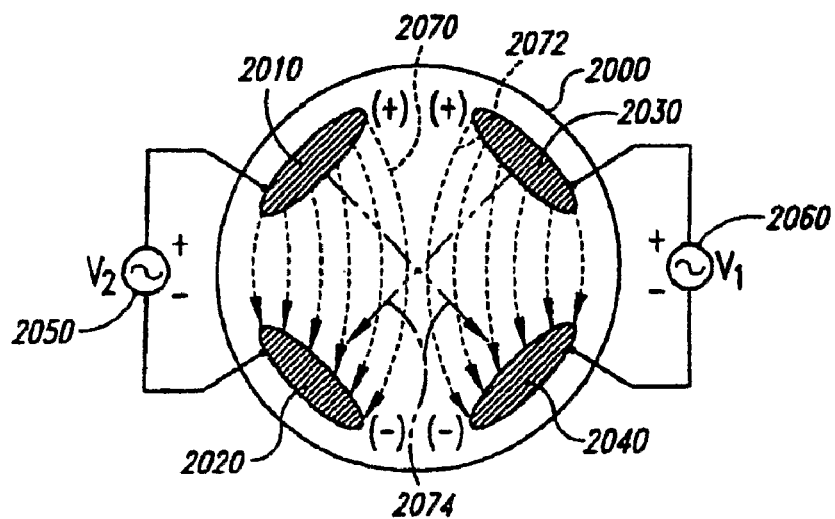
FIG. 20 is a bottom plan view of an electrode configuration for an implantable stimulation device in accordance with yet another embodiment of the invention.

FIG. 20 is a bottom plan view of a stimulation apparatus 2000 in accordance with still another embodiment of the invention. In this embodiment, the stimulation apparatus 2000 includes a first electrode 2010, a second electrode 2020, a third electrode 2030, and a fourth electrode 2040. The first and second electrodes 2010 and 2020 are coupled to a first pulse generator 2050, and the third and fourth electrodes 2030 and 2040 are coupled to a second pulse generator 2060. More specifically, the first electrode 2010 is coupled to the positive terminal and the second electrode 2020 is coupled to the negative terminal of the first pulse generator 2050, and the third electrode 2030 is coupled to the positive terminal and the fourth electrode 2040 is coupled to the negative terminal of the second pulse generator 2060. The first and second electrodes 2010 and 2020 are expected to generate a first electric field 2070, and the third and fourth electrodes 2030 and 2040 are expected to generate a second electric field 2072. It will be appreciated that the ions will be relatively free to move through the brain such that a number of ions will cross between the first and second electric fields 2070 and 2072 as shown by arrows 2074. This embodiment provides control of electric field gradients at the stimulation sites.

FIG. 21 is a bottom plan view of another embodiment of the stimulation apparatus 2000. In this embodiment, the first electrode 2010 is coupled to the positive terminal and the second electrode 2020 is coupled to the negative terminal of the first pulse generator 2050. In contrast to the embodiment shown in FIG. 20, the third electrode 2030 is coupled to the negative terminal and the fourth electrode 2040 is coupled to the positive terminal of the second pulse generator 2070. It is expected that this electrode arrangement will result in a plurality of electric fields between the electrodes. This allows control of the direction or orientation of the electric field.

FIG. 22 is a bottom plan view that schematically illustrates a stimulation apparatus 2200 in accordance with still another embodiment of the invention. In this embodiment, the stimulation apparatus 2200 includes a first electrode 2210, a second electrode 2220, a third electrode 2230, and a fourth electrode 2240. The electrodes are coupled to a pulse generator 2242 by a switch circuit 2250. The switch circuit 2250 can include a first switch 2252 coupled to the first electrode 2210, a second switch 2254 coupled to the second electrode 2220, a third switch 2256 coupled to the third electrode 2230, and a fourth switch 2258 coupled to the fourth electrode 2240. In operation, the switches 2252-2258 can be opened and closed to establish various electric fields between the electrodes 2210-2240. For example, the first switch 2252 and the fourth switch 2258 can be closed in coordination with a pulse from the pulse generator 2242 to generate a first electric field 2260, and/or the second switch 2254 and the third switch 2256 can be closed in coordination with another pulse from the pulse generator 2242 to generate a second electric field 2270. The first and second electric fields 2260 and 2270 can be generated at the same pulse to produce concurrent fields or alternating pulses to produce alternating or rotating fields.

FIG. 23 is a bottom plan view and FIG. 24 is a side elevational view of a stimulation apparatus 2300 in accordance with another embodiment of the invention. In this embodiment, the stimulation apparatus 2300 has a first electrode 2310, a second electrode 2320, a third electrode 2330, and a fourth electrode 2340. The electrodes 2310-2340 can be configured in any of the arrangements set forth above with reference to FIGS. 14-22. The electrodes 2310-2340 also include electrically conductive pins 2350 and/or 2360. The pins 2350 and 2360 can be configured to extend below the pial surface of the cortex. For example, because the length of the pin 2350 is less than the thickness of the cortex 709, the tip of the pin 2350 will accordingly conduct the electrical pulses to a stimulation site within the cortex 709 below the pial surface. The length of the pin 2360 is greater than the thickness of the cortex 709 to conduct the electrical pulses to a portion of the brain below the cortex 709, such as a deep brain region 710. The lengths of the pins are selected to conduct the electrical pulses to stimulation sites below the pia mater 708. As such, the length of the pins 2350 and 2360 can be the same for each electrode or different for individual electrodes. Additionally, only a selected portion of the electrodes and the pins can have an exposed conductive area. For example, the electrodes 2310-2340 and a portion of the pins 2350 and 2360 can be covered with a dielectric material so that only exposed conductive material is at the tips of the pins it will also be appreciated that the configurations of electrodes set forth in FIGS. 14-22 can be adapted to apply an electrical current to stimulation sites below the pia mater by providing pin-like electrodes in a matter similar to the electrodes shown in FIGS. 23 and 24.

Several embodiments of the stimulation apparatus described above with reference to FIGS. 6-24 are expected to be more effective than existing transcranial or subcranial stimulation devices. In addition to positioning the electrodes under the skull, many embodiments of the stimulation apparatus described above also accurately focus the electrical energy in desired patterns relative to the pia mater 708, the dura mater 706, and/or the cortex 709. It will be appreciated that transcranial devices may not accurately focus the energy because the electrodes or other types of energy emitters are positioned relatively far from the stimulation sites and the skull diffuses some of the energy. Also, existing subcranial devices generally merely place the electrodes proximate to a specific nerve, but they do not provide electrode configurations that generate an electrical field in a pattern designed for the stimulation site. Several of the embodiments of the stimulation apparatus described above with reference to FIGS. 6-24 overcome this drawback because the electrodes can be placed against the neurons at the desired stimulation site. Additionally, the electrode configurations of the stimulation apparatus can be configured to provide a desired electric field that is not diffused by the skull 700. Therefore, several embodiments of the stimulation apparatus in accordance with the invention are expected to be more effective because they can accurately focus the energy at the stimulation site.

4. Implantable Stimulation Apparatus with Biasing Elements

FIGS. 25-30 illustrate several embodiments of stimulation apparatus having a biasing element in accordance with a different aspect of the invention. The stimulation apparatus shown in FIGS. 25-30 can be similar to those described above with reference to FIGS. 6-24. Therefore, the embodiments of the stimulation apparatus shown in FIGS. 25-30 can have the same pulse systems, support members and electrode configurations described above with reference to FIGS. 6-24.

Figure 25:
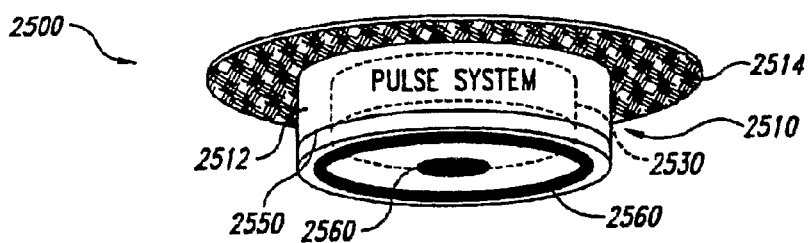
FIG. 25 is an isometric view schematically illustrating a part of an implantable stimulation apparatus with a mechanical biasing element in accordance with an embodiment of the invention.
Figure 26:
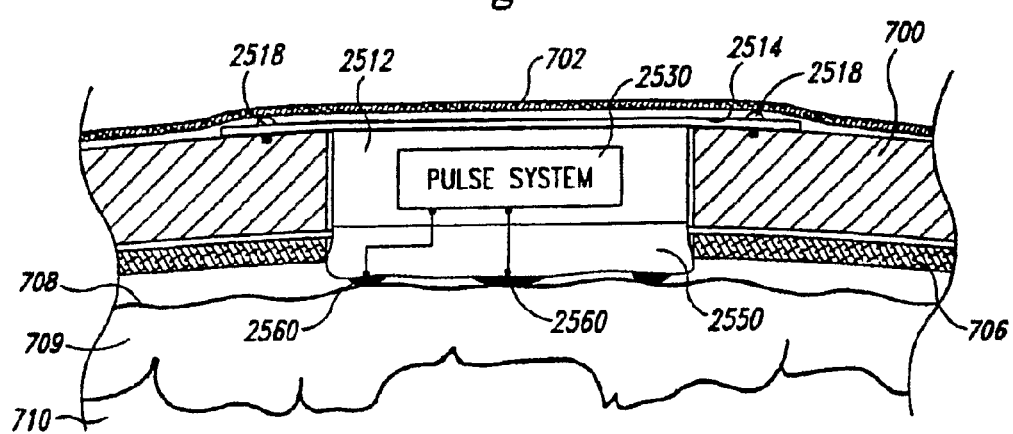
FIG. 26 is a cross-sectional view of a stimulation apparatus having a mechanical biasing element that has been implanted into a skull of a patient in accordance with an embodiment of the invention.

FIG. 25 is an isometric view and FIG. 26 is a cross-sectional view of a stimulation apparatus 2500 in accordance with an embodiment of the invention. In one embodiment, the stimulation apparatus 2500 includes a support member 2510, a pulse-system 2530 carried by the support member 2510, and first and second electrodes 2560 coupled to the pulse system 2530. The support member 2510 can be identical or similar to the support member 610 described above with reference to FIGS. 6 and 7. The support member 2510 can accordingly include a housing 2512 configured to be implanted in the skull 700 and an attachment element 2514 configured to be connected to the skull 700 by fasteners 2518 (FIG. 2), an adhesive, and/or an anchor. The pulse system 2530 can be identical or similar to any of the pulse systems described above with reference to FIGS. 6-13, and the first and second electrodes 2560 can have any of the electrode configurations explained above with reference to FIGS. 14-24. Unlike the stimulation apparatus described above, however, the stimulation apparatus 2500 includes a biasing element 2550 coupled to the electrodes 2560 to mechanically bias the electrodes 2560 away from the support member 2510. In an alternative embodiment, the biasing element 2550 can be positioned between the housing 2512 and the attachment element 2514, and the electrodes 2560 can be attached directly to the housing 2512. As explained in more detail below, the biasing element 2550 can be a compressible member, a fluid filled bladder, a spring, or any other suitable element that resiliently and/or elastically drives the electrodes 2560 away from the support member 2510.

FIG. 26 illustrates an embodiment of the stimulation apparatus 2500 after it has been implanted into the skull 700 of a patient. When the fasteners 2518 are attached to the skull 700, the biasing element 2550 should be compressed slightly so that the electrodes 2560 contact the stimulation site. In the embodiment shown in FIG. 26, the compressed biasing element 2550 gently presses the electrodes 2560 against the surface of the pia mater 708. It is expected that the biasing element 2550 will provide a uniform, consistent contact between the electrodes 2560 and the pial surface of the cortex 709. The stimulation apparatus 2500 is expected to be particularly useful when the implantable device is attached to the skull and the stimulation site is on the pia mater 708 or the dura mater 706. It can be difficult to position the contacts against the pia mater 708 because the distance between the skull 700, the dura mater 706, and the pia mater 708 varies within the cranium as the brain moves relative to the skull, and also as the depth varies from one patient to another. The stimulation apparatus 2500 with the biasing element 2550 compensates for the different distances between the skull 700 and the pia mater 708 so that a single type of device can inherently fit several different patients. Moreover, the stimulation apparatus 2500 with the biasing element 2550 adapts to changes as the brain moves within the skull. In contrast to the stimulation apparatus 2500 with the biasing element 2550, an implantable device that does not have a biasing element 2550 may not fit a particular patient or may not consistently provide electrical contact to the pia mater.

FIGS. 27 and 28 are cross-sectional views of stimulation apparatus in which the biasing elements are compressible members. FIG. 27, more specifically, illustrates a stimulation apparatus 2700 having a biasing element 2750 in accordance with an embodiment of the invention. The stimulation apparatus 2700 can have an integrated pulse system 2530 and electrodes 2560 coupled to the pulse system 2530 in a manner similar to the stimulation apparatus 2500. The biasing element 2750 in this embodiment is a compressible foam, such as a biocompatible closed cell foam or open cell foam. As best shown in FIG. 27, the biasing element 2750 compresses when the stimulation apparatus 2700 is attached to the skull. FIG. 28 illustrates a stimulation apparatus 2800 having a biasing element 2850 in accordance with another embodiment of the invention. The biasing element 2850 can be a compressible solid, such as silicon rubber or other suitable compressible materials. The electrodes 2560 are attached to the biasing element 2850.

FIG. 29 is a cross-sectional view of a stimulation apparatus 2900 having a biasing element 2950 in accordance with another embodiment of the invention. The stimulation apparatus 2900 can have a support member 2910 including an internal passageway 2912 and a diaphragm 2914. The biasing element 2950 can include a flexible bladder 2952 attached to the support member 2910, and the electrodes 2560 can be attached to the flexible bladder 2952. In operation, the flexible bladder 2952 is filled with a fluid 2954 until the electrodes 2560 press against the stimulation site. In one embodiment, the flexible bladder 2952 is filled by inserting a needle of a syringe 2956 through the diaphragm 2914 and injecting the fluid 2954 into the internal passageway 2912 and the flexible bladder.

FIG. 30 is a cross-sectional view of a stimulation apparatus 3000 having a biasing element 3050 in accordance with another embodiment of the invention. In this embodiment, the biasing element 3050 is a spring and the electrodes 2560 are attached to the spring. The biasing element 3050 can be a wave spring, a leaf spring, or any other suitable spring that can mechanically bias the electrodes 2560 against the stimulation site.

Although several embodiments of the stimulation apparatus shown in FIGS. 25-30 can have a biasing element and any of the pulse systems set forth above with respect to FIGS. 6-13, it is not necessary to have a pulse system contained within the support member. Therefore, certain embodiments of implantable stimulation apparatus in accordance with the invention can have a pulse system and/or a biasing member in any combination of the embodiments set forth above with respect to FIGS. 6-30.

5. Implantable Stimulation Apparatus with External Pulse Systems

Figure 31:
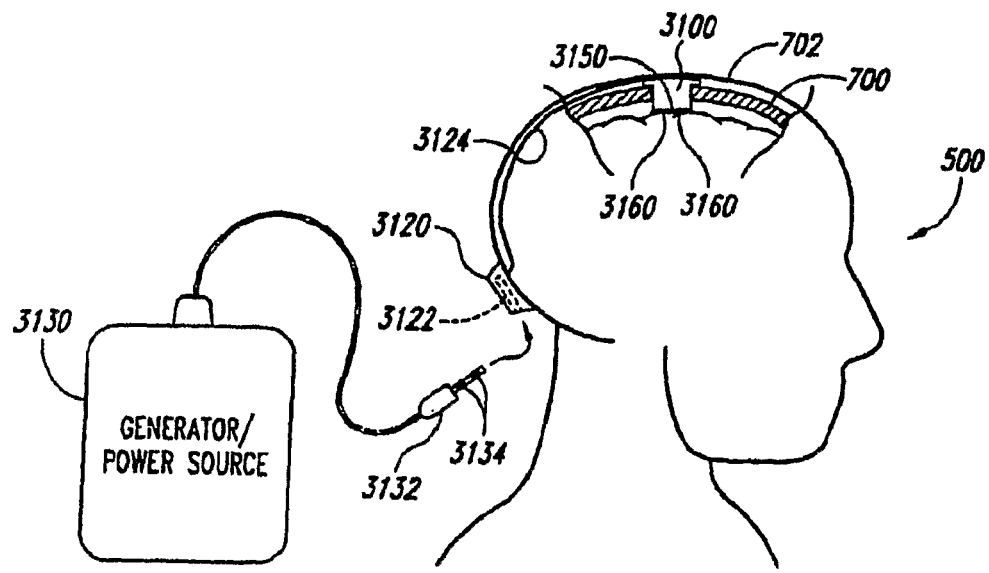
FIG. 31 is a cross-sectional view schematically illustrating a portion of an implantable stimulation apparatus having an external power source and pulse generator in accordance with an embodiment of the invention.

FIGS. 31-35 are schematic cross-sectional views of various embodiments of implantable stimulation apparatus having external pulse systems. FIG. 31, more specifically, illustrates an embodiment of a stimulation apparatus 3100 having a biasing element 3150 to which a plurality of electrodes 3160 are attached in a manner similar to the stimulation apparatus described above with reference to FIGS. 25-30. It will be appreciated that the stimulation apparatus 3100 may not include the biasing element 3150. The stimulation apparatus 3100 can also include an external receptacle 3120 having an electrical socket 3122 and an implanted lead line 3124 coupling the electrodes 3160 to contacts (not shown) in the socket 3122. The lead line 3124 can be implanted in a subcutaneous tunnel or other passageway in a manner known to a person skilled and art.

The stimulation apparatus 3100, however, does not have an internal pulse system carried by the portion of the device that is implanted in the skull 700 of the patient 500. The stimulation apparatus 3100 receives electrical pulses from an external pulse system 3130. The external pulse system 3130 can have an electrical connector 3132 with a plurality of contacts 3134 configured to engage the contacts within the receptacle 3120. The external pulse system 3130 can also have a power supply, controller, pulse generator, and pulse transmitter to generate the electrical pulses. In operation, the external pulse system 3130 sends electrical pulses to the stimulation apparatus 3100 via the connector 3132, the receptacle 3120, and the lead line 3124.

Figure 32:
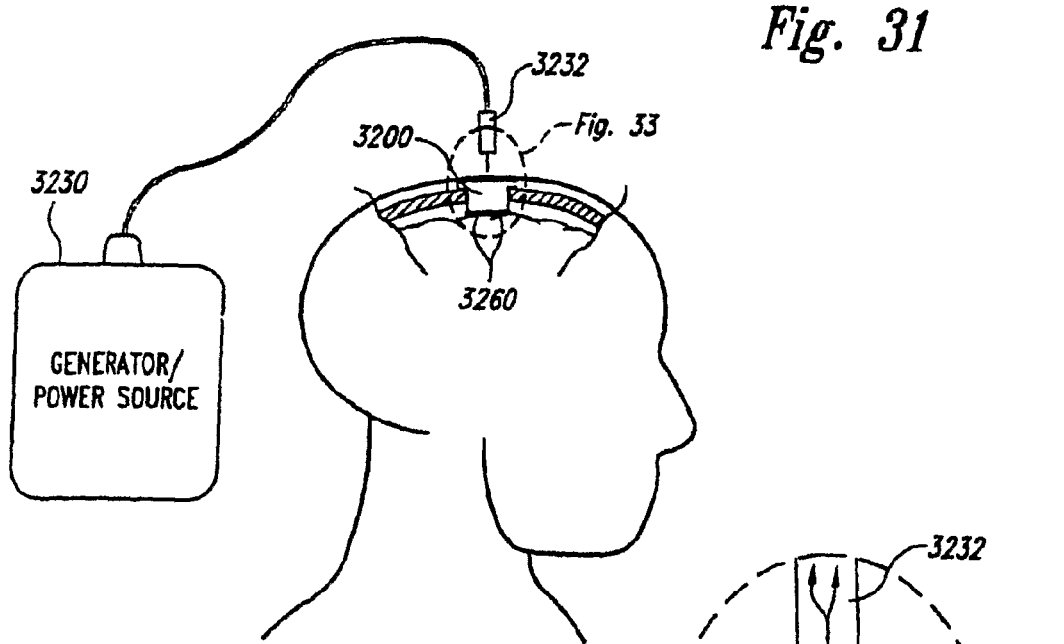
FIG. 32 is a cross-sectional view schematically illustrating a portion of an implantable stimulation apparatus having an external power source and pulse generator in accordance with another embodiment of the invention.
Figure 33:
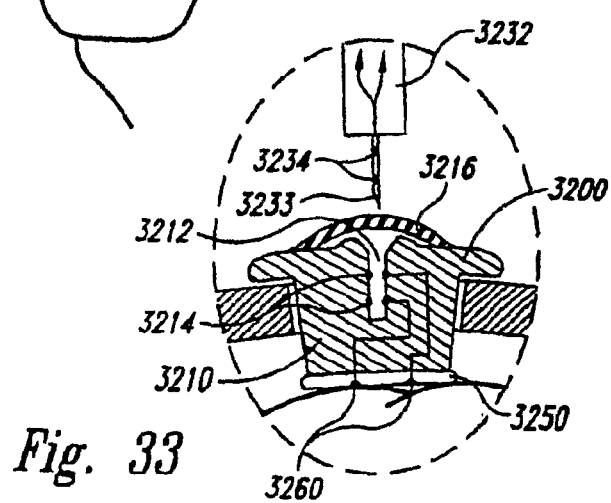
FIG. 33 is a cross-sectional view illustrating in greater detail a portion of the implantable stimulation apparatus of FIG. 32.

FIGS. 32 and 33 illustrate an embodiment of a stimulation apparatus 3200 for use with an external pulse system in accordance with another embodiment of the invention. Referring to FIG. 33, the stimulation apparatus 3200 can include a support structure 3210 having a socket 3212, a plurality of contacts 3214 arranged in the socket 3212, and a diaphragm 3216 covering the socket 3212. The stimulation apparatus 3200 can also include a biasing element 3250 and a plurality of electrodes 3260 attached to the biasing element 3250. Each electrode 3260 is directly coupled to one of the contacts 3214 within the support structure 3210. It will be appreciated that an alternative embodiment of the stimulation apparatus 3200 does not include the biasing element 3250.

Referring to FIGS. 32 and 33 together, the stimulation apparatus 3200 receives the electrical pulses from an external pulse system 3230 that has a power supply, controller, pulse generator, and pulse transmitter. The external pulse system 3230 can also include a plug 3232 having a needle 3233 (FIG. 33) and a plurality of contacts 3234 (FIG. 33) arranged on the needle 3233 to contact the internal contacts 3214 in the socket 3212. In operation, the needle 3233 is inserted into the socket 3212 to engage the contacts 3234 with the contacts 3214, and then the pulse system 3230 is activated to transmit electrical pulses to the electrodes 3260.

Figure 34:
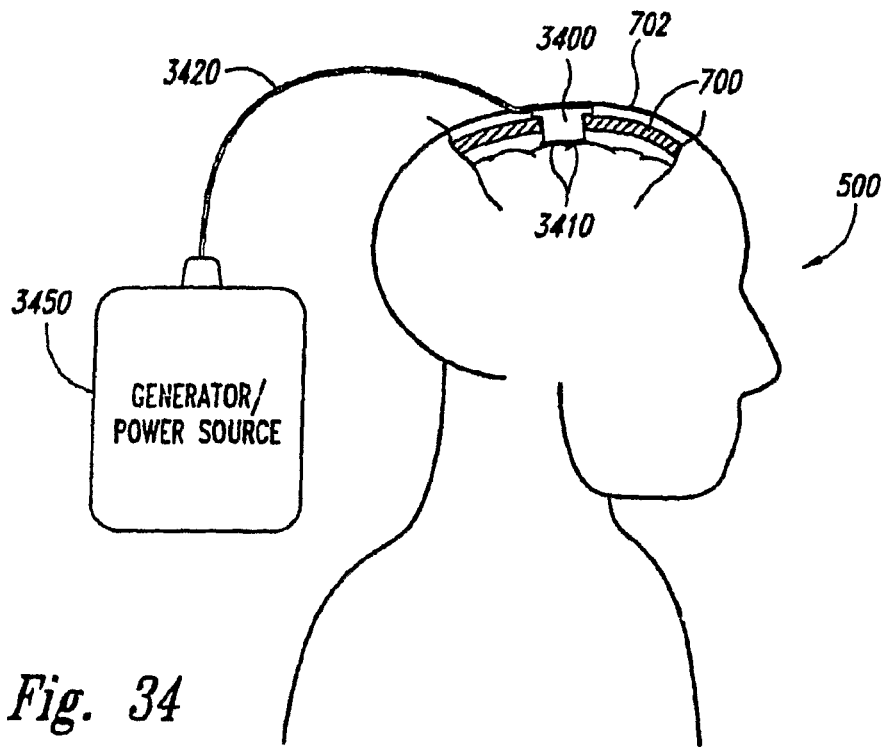
FIG. 34 is a cross-sectional view schematically illustrating a portion of an implantable stimulation apparatus and an external controller in accordance with another embodiment of the invention.
Figure 35:
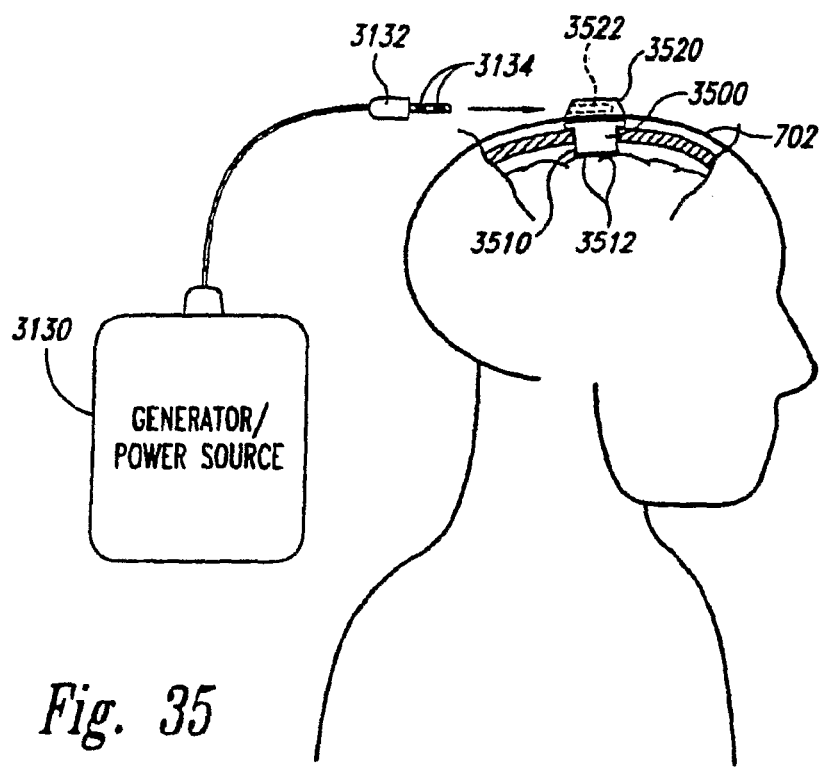
FIG. 35 is a cross-sectional view schematically illustrating a portion of an implantable stimulation apparatus and an external controller in accordance with yet another embodiment of the invention.

FIGS. 34 and 35 illustrate additional embodiments of stimulation apparatus for use with external pulse systems. FIG. 34 illustrates an embodiment of a stimulation apparatus 3400 having electrodes 3410 coupled to a lead line 3420 that extends under the scalp 702 of the patient 500. The lead line 3420 is coupled to an external pulse system 3450. FIG. 35 illustrates an embodiment of a stimulation apparatus 3500 having a support member 3510, electrodes 3512 coupled to the support member 3510, and an external receptacle 3520 mounted on the scalp 702. The external receptacle 3520 can also be connected to the support member 3510. The external receptacle 3520 can have a socket 3522 with contacts (not shown) electrically coupled to the electrodes 3512. The stimulation apparatus 3500 can be used with the external pulse system 3130 described above with reference to FIG. 31 by inserting the plug 3132 into the socket 3522 until the contacts 3134 on the plug 3132 engage the contacts within the socket 3522.

6. Alternate Embodiments of Implantable Stimulation Apparatus

Figure 36:
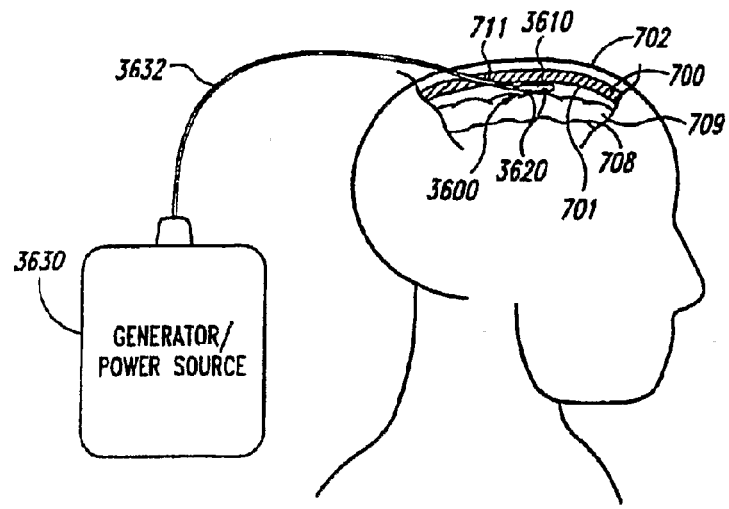
FIG. 36 is a cross-sectional view schematically illustrating a portion of an implantable stimulation apparatus in accordance with yet another embodiment of the invention.

FIG. 36 is a schematic cross-sectional view of an implantable stimulation apparatus 3600 in accordance with another embodiment of the invention. In one embodiment, the stimulation apparatus 3600 has a support structure 3610 and a plurality of electrodes 3620 coupled to the support structure 3610. The support structure 3610 can be configured to be implanted under the skull 700 between an interior surface 701 of the skull 700 and the pial surface of the brain. The support structure 3610 can be a flexible or compressible body such that the electrodes 3620 contact the pia mater 708 when the stimulation apparatus 3600 is implanted under the skull 700. In other embodiments, the support structure 3610 can position the electrodes 3620 so that they are proximate to, but not touching, the pia mater 708.

In one embodiment, the stimulation apparatus 3600 can receive electrical pulses from an external controller 3630. For example, the external controller 3630 can be electrically coupled to the stimulation apparatus 3600 by a lead line 3632 that passes through a hole 711 in the skull 700. In an alternative embodiment, the stimulation apparatus 3600 can include an integrated pulse system similar to the pulse systems described above with reference to FIGS. 6-13. Such an embodiment of the stimulation apparatus 3600 can accordingly use a wireless external control unit. It will be appreciated that the electrodes 3620 of the stimulation apparatus 3600 can have several of the electrode configurations described above with reference to FIGS. 14-24.

Figure 37:
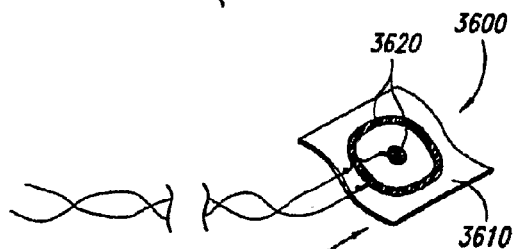
FIG. 37 is an isometric view.
Figure 38:
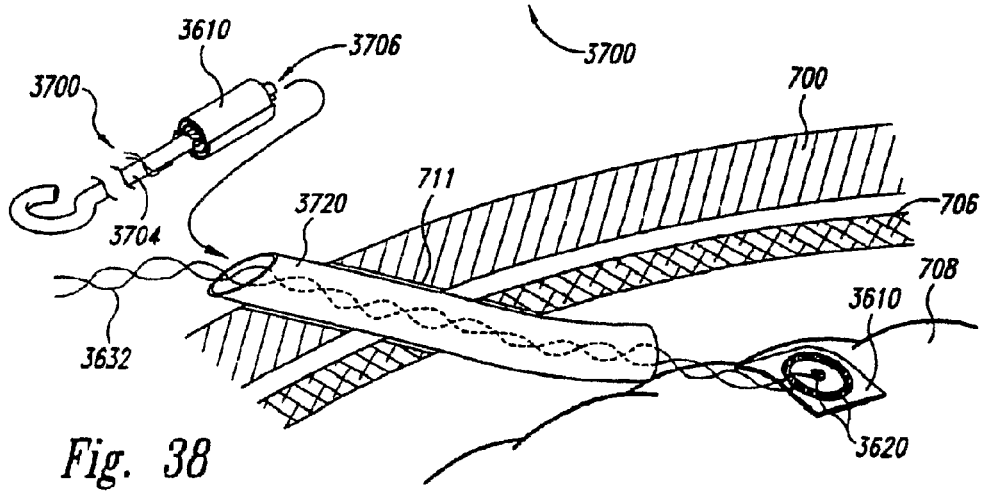
FIG. 38 is a cross-sectional view illustrating an implantable stimulation apparatus in accordance with an embodiment of the invention.

FIGS. 37 and 38 illustrate one embodiment of the implantable stimulation apparatus 3600. Referring to FIG. 37, the support structure 3610 can be a flexible substrate and the electrodes 3620 can be conductive elements that are printed onto the flexible substrate. The stimulation apparatus 3600, for example, can be manufactured in a manner similar to flexible printed circuit assemblies that are used in electrical components. The stimulation apparatus 3600 can be implanted under the skull 700 using an insertion tool 3700. In one embodiment, the insertion tool 3700 has a handle 3702 and a shaft 3704 projecting from the handle 3702. The shaft 3704 can have a slot 3706 configured to receive a flat portion of the support member 3610. Referring to FIG. 38, the support member 3610 is wrapped around the shaft 3704, and then the stimulation apparatus 3600 is passed to a tube 3720 positioned in the hole 711 through the scalp 700 and the dura mater 706. After the stimulation apparatus 3600 has been passed through the tube 3720, it is unfurled to place the electrodes 3620 at least proximate to the pia mater 708. The electrodes 3620 can be coupled to an external controller by the lead lines 3632.

Figure 39:
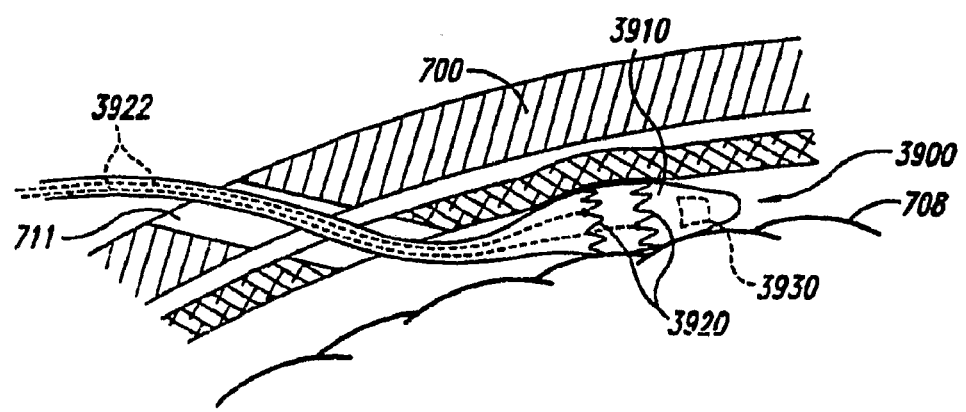
FIG. 39 is a cross-sectional view illustrating an implantable stimulation apparatus in accordance with yet another embodiment of the invention.

FIG. 39 illustrates another embodiment of an implantable stimulation apparatus 3900 that is also configured to be positioned between the skull 700 and the pia mater 708. In one embodiment, the stimulation apparatus 3900 can include a support member 3910 and a plurality of electrodes 3920 coupled to the support member 3910. The electrodes 3920 can be coupled to individual lead lines 3922 to connect the electrodes 3920 to an external pulse system. In an alternative embodiment, an integrated pulse system 3930 can be carried by the support member 3910 so that the electrodes 3920 can be coupled directly to the integrated pulse system 3930 without external lead lines 3922. The support member 3910 can be a resiliently compressible member, an inflatable balloon-like device, or a substantially solid incompressible body. In the particular embodiment shown in FIG. 39, the support member 3910 is an inflatable balloon-like device that carries the electrodes 3920. In operation, the stimulation apparatus 3900 is implanted by passing the distal end of the support member 3910 through the hole 711 in the skull 700 until the electrodes 3920 are positioned at a desired stimulation site.

FIGS. 40A and 40B illustrate another embodiment of an implantable stimulation apparatus 4000 that is also configured to be positioned between the skull 700 and the pia mater 708 (shown in FIG. 39) or dura mater. In this embodiment, the implantable stimulation apparatus 4000 includes a support member or implantable medium 4010 and an electrode array having a plurality of electrodes 4020 that are carried by the support member 4010. The electrodes 4020 can be coupled to individual lead lines 4022 that are connected to an external pulse system. The support member 4010 can be a flexible body that is configurable between a first shape for insertion through a hole in the patient and a second shape that is larger than the first shape to cover a surface area on the cortex or another portion of the patient. For example, the support member 4010 can be inserted through the hole 711 (FIG. 39) when, it is in the first shape.

The embodiment of the support member 4010 shown in FIGS. 40A and 40B is an inflatable bladder or balloon that can be filled with a fluid, such as a saline solution or another biocompatible fluid. FIG. 40A shows the support member 4010 in a first shape or configuration for insertion through a hole in the patient. The first shape typically has a maximum dimension of approximately 1-5 mm so that the stimulation apparatus 4000 can be inserted through a small hole in the patient. FIG. 40B illustrates the support structure 4010 in a second shape that is larger than the first shape to cover an adequate area on the surface of the cortex. The expanded or deployed shape can be approximately 1.0-10.0 $cm^2$. In a particular embodiment shown in FIG. 40B, the support member 4010 expands into the second shape so that it is relatively flat. As a result, the support member 4010 is a flexible body that can be configured from a first shape for insertion through a small hole in the patient to a second shape that is larger than the first shape so that the electrodes 4020 can contact a relatively large surface area on the cortex or dura relative to the size of the insertion hole.

The stimulation apparatus 4000 is expected to provide electrical stimulation to a large surface area of the cortex, spine, or other body part without having to form a large hole in the patient. In the case of providing electrical stimulation to the cortex, the stimulation apparatus 4000 can be inserted through a hole in the patient's skull having a diameter of approximately 1-5 mm, and then it can be inflated to cover an area of approximately 1-10 $cm^2$ on the cortex of the patient. Using such a small insertion hole is beneficial because the small craniectomy is much less traumatic to the patient compared to a larger craniectomy of approximately 2-5 cm in diameter. As a result, it is expected that the lesser invasive stimulation apparatus 4000 will be more beneficial for cortical, spinal or other types of electrical stimulation.

FIGS. 41A and 41B illustrate another embodiment of an implantable stimulation apparatus 4100 that is configured to be positioned between the skull 700 and the pia mater 708 (FIG. 39) or dura mater. In this embodiment, the stimulation apparatus 4100 includes a support member 4110 and an electrode array having a plurality of electrodes 4120 carried by the support member 4110. The support member 4110 can be a compressible foam that maintains a compressed configuration or a first shape for insertion through a hole in the patient when it is dry, and then expands to a second shape when it becomes wet. The support member 4110 can be implanted into the patient through a small hole when it is in the compressed configuration, and then saline can be injected into the support member 4110 to expand it into a expanded configuration. In operation, both the stimulation device 4000 shown in FIGS. 40A and 40B and the stimulation apparatus 4100 shown in FIGS. 41A and 41B also press the electrodes against the pia mater 708 (FIG. 39) or dura because they can be expanded to the extent that they press against the inner surface of the skull 700 to provide a downforce against the pia mater 708 or dura.

FIGS. 42A and 42B illustrate yet another embodiment of an implantable stimulation apparatus 4200 in accordance with another embodiment of the invention. The stimulation apparatus 4200 can include a support member 4210 and an electrode array having a plurality of electrodes 4220 carried by the support member 4210. The support member 4210 can be a flexible body, such as a sheath or other type of covering that is attached to an introducer 4230, such as a catheter. The stimulation apparatus 4200 further includes a mechanical actuator 4240 that includes a plurality of fingers 4242 that can move between a first or insertion position (shown in FIG. 42A) and a second or deployed position (shown in FIG. 42B). The mechanical actuator 4240 can further include a driver 4244 having a cavity 4246 and distal openings 4248. The fingers 4242 can be coupled to a support 4250 that extends through the cavity 4246 of the driver 4244. For example, the fingers 4242 can be coupled to the support 4250 by a joint 4252, such as a weld, pin, or other type of joint that allows the outer fingers to pivot with respect to the support 4250. The fingers 4242 pass through the distal openings 4248 in the driver so that axial movement of the driver (shown by arrow A) causes the outer fingers 4242 to rotate either away from or toward the central finger 4242.

The stimulation apparatus 4100 operates by inserting the introducer 4230 through a small hole in the patient when the fingers 4242 are collapsed together in a first configuration (e.g., the insertion configuration shown in FIG. 42A). After appropriately positioning the distal portion of the stimulation apparatus 4200 in the patient, the driver 4244 is moved toward the proximal end so that the edge of the side distal openings 4248 spreads the outer fingers 4242 outwardly away from the central finger 4242. The fingers 4242 accordingly expand the support member 4210 so that the electrodes 4220 can cover a larger surface area of the patient. The electrodes 4220 are typically coupled to a plurality of leads (not shown) that can extend through the introducer 4230.

FIGS. 43A and 43B illustrate yet another embodiment of an implantable stimulation apparatus 4300 that can be configured to be positioned between the skull 700 and the pia mater 708 or dura mater through a small insertion hole 711 (FIG. 39). The stimulation apparatus 4300 can include a support member 4310, an electrode array having a plurality of electrodes 4320 carried by the support member 4310, and a mechanical actuator 4340 extending through the support member 4310. The support member 4310 can be a sheath or a solid, flexible body that surrounds the mechanical actuator 4340, and the electrodes 4320 can be carried on the surface of the support member 4310. The mechanical actuator 4340 in this embodiment is a shape memory element that automatically conforms into a predetermined shape (e.g., the memory shape) at a certain temperature. For example, the mechanical actuator 4340 can be a nitinol filament that automatically moves into the predetermined memory shape at approximately the body temperature of humans. The shape memory filament can be a spring with a stiff wire that is coiled in one configuration and at least partially uncoiled in another configuration.

FIG. 43A shows the stimulation apparatus 4300 in the insertion or first configuration in which the mechanical actuator 4340 is a nitinol element that has been bent from a spiral memory shape into a straight line. This configuration accordingly allows the stimulation apparatus 4300 to be inserted through a small insertion hole in the patient. FIG. 43B illustrates the stimulation apparatus 4300 in a deployed configuration or second shape in which the mechanical actuator 4340 is a nitinol element that has a memory shape in the form of a spiral. In operation, therefore, the stimulation apparatus 4300 can be inserted through a small insertion hole in the insertion configuration (FIG. 43A), and then the heat of the patient causes the mechanical actuator 4340 to return to its spiral configuration. The support member 4340 accordingly flexes with the mechanical actuator 4340 after it has been inserted into the patient. This allows the insertion device 4340 to cover a well-defined area of the cortex, spine, or other body part of the patient for electrical stimulation.

Figure 44A:
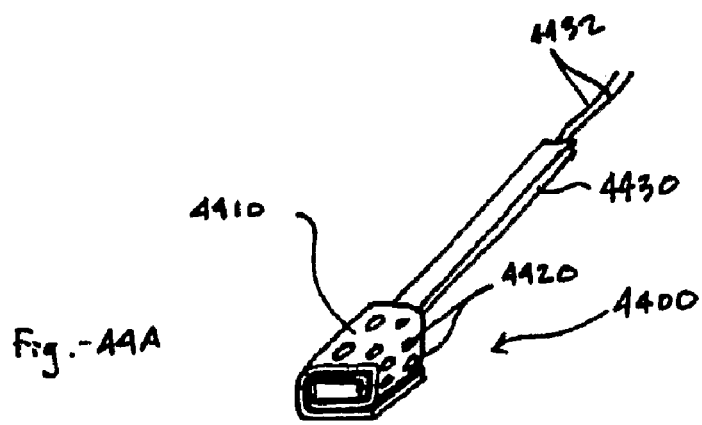
FIGS. 44A and 44B illustrate an implantable stimulation apparatus in accordance with still another embodiment of the invention.
Figure 44B:
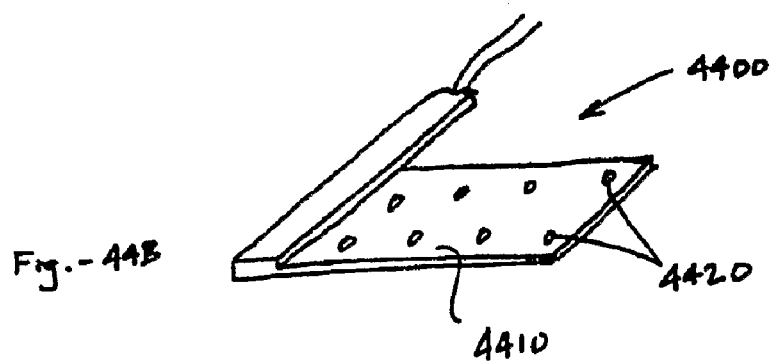

FIGS. 44A and 44B illustrate an implantable stimulation apparatus 4400 that can be rolled up in an insertion configuration and unfurled in a deployed configuration. Referring to FIG. 44A, the insertion apparatus 4400 includes a flexible support member 4410 and an electrode array having a plurality of electrodes 4420 carried by the support member 4410. The support member 4410 can be a flexible sheet coupled to the distal end of insertion member 4430. The electrodes 4420 can be coupled to electrical leads 4432 that extend through the insertion member 4430. FIG. 44A shows the stimulation apparatus 4400 in an insertion configuration in which the support member 4410 is rolled about the insertion member 4430, and FIG. 44B illustrates the stimulation apparatus 4400 in a deployed configuration in which the support member 4410 has been unfurled to cover a larger surface area of the cortex, spinal column, or other body part of the patient. The operation and advantages of the stimulation apparatus 4400 are expected to be similar to the insertion apparatus 3600 described above with reference to FIGS. 37 and 38.

Figure 45:
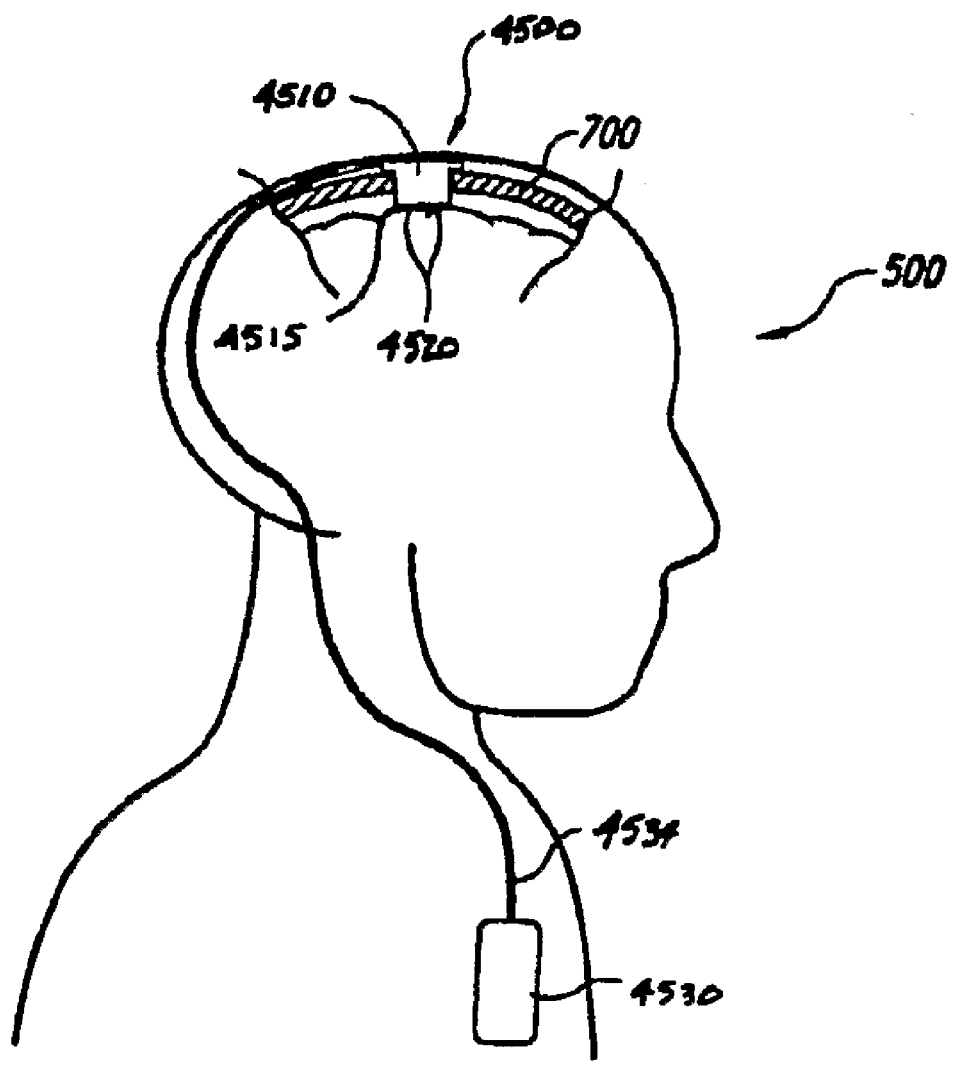
FIG. 45 is a schematic illustration of an implantable stimulation apparatus in accordance with an embodiment of the invention.

FIG. 45 is a schematic illustration of a stimulation apparatus 4500 together with an internal pulse system 4530 in accordance with another embodiment of the invention. The stimulation apparatus 4500 can include a support member 4510, a biasing element 4515 carried by the support member 4510, and a plurality of electrodes 4520 carried by the biasing element 4515. The internal pulse system 4530 can be similar to any of the integrated pulse systems described above with reference to FIGS. 6-13, but the internal pulse system 4530 is not an integrated pulse system because it is not carried by the housing 4510. The internal pulse system 4530 can be coupled to the electrodes 4520 by a cable 4534. In a typical application, the cable 4534 is implanted subcutaneously in a tunnel from a subclavicular region, along the back of the neck, and around the skull. The stimulation apparatus 4500 can also include any of the electrode configurations described above with reference to FIGS. 14-24.

C. Systems and Methods for Applying Regulatable Mechanical Forces

Regulatable mechanical force applied to neural tissues can also be used to treat neurological disorders, with or without electrical stimulation. Many of the foregoing devices can be used to provide such a force. In other embodiments, other devices can be used to provide such forces. It has been found that mechanical force application on the surface of the brain (including subdural applications) can lead to a striking and long lasting (several weeks to months) improvement in tremor of patients with essential tremor. The major benefit is expected to be predominantly due to the mechanical force, but the benefit may also be supplemented with (and/or partially attributable to) electrical stimulation. A representative process for treatment can include:

(1) Functional imaging via fMRI, PET, SPECT, MEG, EEG and/or another method to localize a brain target;
(2) Applying a mechanical device to the target in the cortex, subcortical structures, spinal cord or the peripheral nervous system; and
(3) Applying a force (e.g., intermittently applying force in a titrated and tightly controlled fashion) through inflation or mechanical expansion/deformation of the device, leading to the application of force or mechanical distortion of neural elements.

The force/mechanical distortion can be measured and monitored to a specified level to obtain therapeutic benefit and avoid permanent damage, for example, via a feedback mechanism.

In particular embodiments, the system can have a closed loop arrangement where the force applied is based on an input signal, for example tremor, EEG signal etc., which is transmitted to a processor and a signal output generator to the mechanical device. The force applied can be measured and monitored to specified levels. The therapy may include cycling-on-off-on-off of variable duration cycles. The device may also be coupled to a supplemental device to deliver electrical stimulation and/or infuse drugs. The adjunct of mechanical force can also reduce the need for stimulation or reduce output requirements. This in turn can result in longer battery life and/or smaller batteries in devices that include electrical stimulation capabilities. Indications include the treatment of tremors of various etiologies (PD, ET, MS, Cerebellar, Post traumatic), chorea, dyskinesias, tics, myoclonus, dystonia, epilepsy (particularly focal epilepsies in eloquent areas), psychiatric disorders, and pain.

Figure 46:
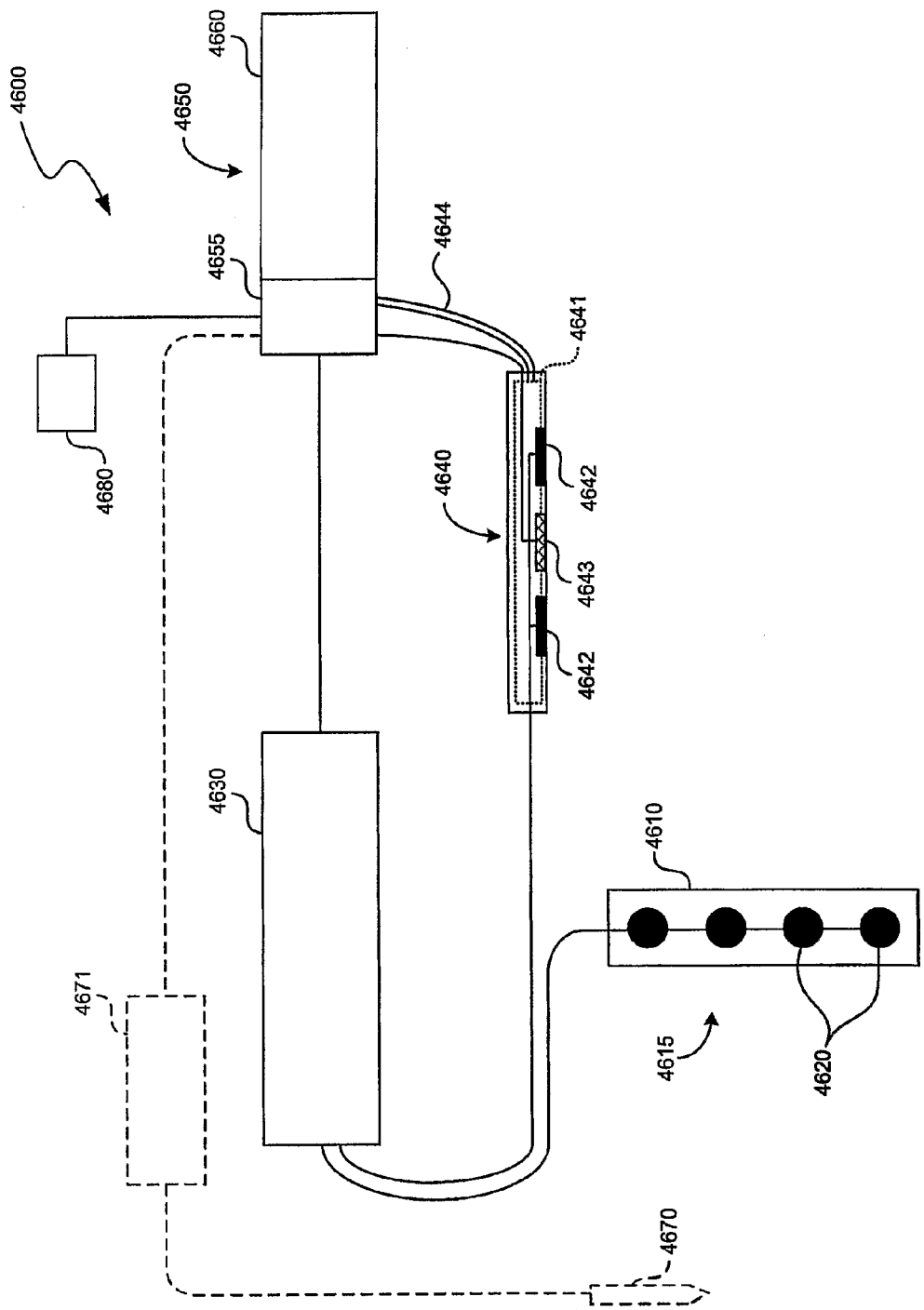
FIG. 46 is a schematic illustration of an apparatus configured to apply a mechanical force, including intermittent mechanical forces, to neural tissue.

FIG. 46 is a schematic illustration of a treatment apparatus 4600 that can be used to apply persistent and/or intermittent mechanical forces to a patient's neural tissue in accordance with an embodiment of the invention. The treatment apparatus 4600 can include a force delivery device 4640 that is implanted at least proximate to the target neural tissue to apply a mechanical force to the tissue. The force delivery device 4640 can be coupled to an actuator 4650 with a communication link 4644. The actuator 4650 can include a controller 4655 that directs the actuator 4650 to activate the force delivery device 4640 at selected times for selected intervals.

As described above, the treatment apparatus 4600 can optionally supplement the mechanical force provided by the force delivery device 4640 with electrical stimulation and/or drug infusion and/or other substance infusion. Accordingly, the treatment apparatus 4600 can optionally include an electrical stimulation device 4615 having one or more electrodes 4620 carried by a support 4610. The electrodes 4620 can be coupled to a pulse generator 4630 to provide electrical stimulation in accordance with any of the parameters described in greater detail above with reference to previous Figures. The electrodes 4620 can provide stimulation at or near the surface of the target neural structure (e.g., epidurally or subdurally). In other embodiments, the electrodes can be positioned at an intraparenchymal location, e.g., at a subcortical or deep brain location. Representative electrode configurations were described above, including with reference to FIGS. 23 and 24. In still further embodiments, electrical stimulation can be provided at both surface and intraparenchymal locations. In any of these embodiments, the electrical stimulation can be selected to have an inhibitory effect, e.g., when the neurological, psychiatric and/or physiological dysfunction is characterized by an excessive or abnormal pattern of activities.

Conversely, the electrical stimulation can be selected to have an excitatory effect in cases where the target brain (or other neural) tissue is underactive.

An optional drug infusion device 4670 can be implanted in the patient to provide the patient with drugs supplied from a drug reservoir 4671. The drug reservoir 4671 and/or the pulse generator 4630 can be coupled to the controller 4655. Accordingly, the controller 4655 can coordinate the delivery of the optional electrical stimulation and/or drug infusion with the delivery of mechanical forces provided by the force delivery device 4640. The drug infusion device 4670 and reservoir 4671 are shown schematically in FIG. 46. In some embodiments, these components or portions of these components can be located external to the patient's body, and in other embodiments, these components or portions of these components can be implanted in the patient's body. For example, the components can include a fully implantable drug delivery pump. Accordingly, a single apparatus 4600 can include an implant that provides any of the following therapies, singly or in combination: electrical therapy, drug therapy and mechanical force therapy. If multiple therapies are to be provided at a single target location, the apparatus 4600 can include a single implantable element. If one or more therapies are to be applied at multiple locations, the apparatus 4600 can include multiple implantable elements. In particular embodiments, the drug infusion device 4670 can be configured to provide drugs proximate to the surface of a target neural structure, and in other embodiments, the drugs can be provided to intraparenchymal locations. As with the electrical stimulation described above, drugs may also be provided to both locations in some embodiments.

The drug selected for application to the patient can include a neurotrophic factor (e.g., GDNF) or another substance. As with the electrical stimulation described above, the drug can be selected to have an inhibitory or excitatory effect on the target neural tissue. Suitable inhibitory drugs include inhibitory neurotransmitters and analogues for example, gamma amino butyric acid (GABA) and muscimol, (including components that alter the effective levels of such drugs), inhibitory peptides, and/or local anesthetics, such as lidocaine or marcaine. Suitable excitatory drugs include excitatory neurotransmitters and analogues, or compounds that increase the effective levels of such molecules and peptides.

In a particular embodiment, the force delivery device 4640 can include an inflatable bladder 4641, and the actuator 4650 can include a reservoir 4660 with fluid (e.g., liquid) suitable for inflating the bladder 4641. Accordingly, the communication link 4644 can include a fluid conduit for transmitting fluid back and forth between the bladder 4641 and the reservoir 4660 as the bladder 4641 is inflated and deflated. The force applied by the bladder 4641 to the adjacent neural tissue may be provided by direct contact between the bladder 4641 and the adjacent tissue, or the bladder 4641 may carry one or more electrical contacts 4642 that press against the adjacent neural tissue when the bladder 4641 is inflated. The electrical contacts 4642 can optionally be coupled to the pulse generator 4630 to provide electrical stimulation to the neural tissue, in addition to providing a mechanical force against the neural tissue.

In any of the foregoing arrangements, the bladder 4641 or other forcing element of the force delivery device 4640 can provide a pre-selected maximum force. In a particular embodiment, the pre-selected maximum force can produce a pressure of from about 26.5 gm/cm$^2$ to about 30 gm/cm$^2$. For example, these pressure levels can be used when the force is applied more or less continuously (e.g., for an hour or more). The maximum force applied to a patient in a given treatment regimen may depend upon the time the force is applied. For example, if the force is applied intermittently (e.g., for a period of 10 minutes or less), the maximum pressure can be roughly twice what it is for continuous applications (e.g., from about 53 gm/cm$^2$ to about 60 gm/cm$^2$). In other embodiments, the pressures and associated forces can have other values, so long as the overall pressure applied to the adjacent neural tissue does not exceed acceptable thresholds.

In particular embodiments, the treatment apparatus 4600 can also include a sensor 4643 positioned to measure a characteristic of the force delivery device 4640 and/or a characteristic of the patient in whom the force delivery device 4640 is implanted, and provide a feedback signal to the controller 4655. For example, in a particular embodiment, the sensor 4643 can include a strain gauge or other force or pressure measurement device positioned to measure a quantity corresponding to the force applied by the force delivery device 4640. In cases where electrical and/or drug-based therapy is provided, the sensor 4643 can include an electrical and/or chemical sensor. When the sensor 4643 includes a force sensor, it can transmit to the controller 4655 a signal corresponding to the applied force. The controller 4655 can then direct the actuator 4650 to adjust the force provided by the force delivery device 4640 to a selected value or in accordance with a selected schedule that is within pre-determined limits. The controller 4655 can also include a timing component and can accordingly control the duration over which forces are applied by the force delivery device 4640. As discussed above, the duration may depend upon the force applied, and in general, the higher the force applied, the shorter the duration over which the force is applied.

The controller 4655 can be configured to direct the force delivery device 4640 to apply forces to the patient intermittently and over multiple force delivery cycles. Accordingly, the controller 4655 can include a computer-readable medium (e.g., a programmable medium) having appropriate, automatically executable instructions. The instructions can, in at least some cases, be updated and/or overridden by a practitioner and/or a patient. It is believed that in at least some embodiments, automatically providing intermittent mechanical forces to the adjacent neural tissue can have enhanced beneficial effects for the patient, as compared with a patient having either no mechanical force applied to the neural tissue or a persistent mechanical force applied to the neural tissue. In particular embodiments, the controller 4655 can be configured to control the force applied by the force delivery device 4640 to change between a first state (e.g., applying a relatively high force) and a second state (e.g., applying no force or a lower force). The force can be constant in either or both states. In other embodiments, the controller 4655 can vary the force applied by the force delivery device 4640 in either or both states, in accordance with a variety of schedules (e.g., by gradually increasing the force, gradually decreasing the force, increasing the force then decreasing the force, and/or directing cycles of increasing and decreasing force). The manner in which the force is applied when the force delivery device 4640 is in the first state can vary from one "state 1-state 2" cycle to the next, as can the force applied in the second state. In any of these embodiments, the average force or pressure applied when the force delivery device 4640 is in the first state can be higher than when the force delivery device 4640 is in the second state.

In addition to the expected benefit for the patient, the application of mechanical force in an intermittent manner can reduce the overall power consumed by the treatment apparatus 4600 and can accordingly extend the life of a battery or other power supply used to power the apparatus 4600. This arrangement can be particularly advantageous when the power supply is implanted in the patient, so as to reduce the frequency with which the patient is inconvenienced by periodic updates (e.g., recharges) of the power supply.

As noted above, the controller 4655 can also act to coordinate the activity of the force delivery device 4640 and the (optional) drug infusion device 4670 and/or electrical stimulation device 4615. For example, in some embodiments, the controller 4655 can direct the drug infusion device 4670 to provide drugs while the force delivery device 4640 is in the first state. In other embodiments, the controller 4655 can direct the drug infusion device 4670 to provide a drug infusion only when the force delivery device 4640 is in the second state. Similarly, the controller 4655 can direct the electrical stimulation device 4615 to be active when the force delivery device 4640 is in the first state, the second state, or both states.

The electrical stimulation device 4615 can provide a variety of functions that support treatment of the patient. For example, the electrical stimulation device 4615 can provide a conductive return path for electrical stimulation provided by the electrical contact(s) 4642 carried by the force delivery device 4640. Accordingly, the electrical stimulation device 4615 can be positioned remote from the target neural tissue. In another embodiment, the electrical stimulation device 4615 can provide electrical stimulation proximate to the target neural tissue and/or to tissue at a different stimulation site. In still another embodiment, the electrical stimulation device 4615 can provide feedback signals to the controller 4655 by detecting electrical activity associated with the patient's neural response to the imposition of mechanical forces from the force delivery device 4640.

In still further embodiments, feedback can be provided manually by the patient via a patient-controlled feedback device 4680. This input device 4680 can allow the patient to selectively change the state of the force delivery device 4640, the electrical stimulation device 4615, and/or the drug infusion device 4670. Further details of embodiments in which the patient can provide such inputs are described below with reference to FIGS. 49A and 49B.

FIGS. 47-50 are flow diagrams illustrating methods for treating patients in accordance with particular embodiments of the invention. Many of these methods may be carried out by devices generally similar to that described above with reference to FIG. 46 and/or devices described with reference to other previously discussed Figures.

Figure 47:
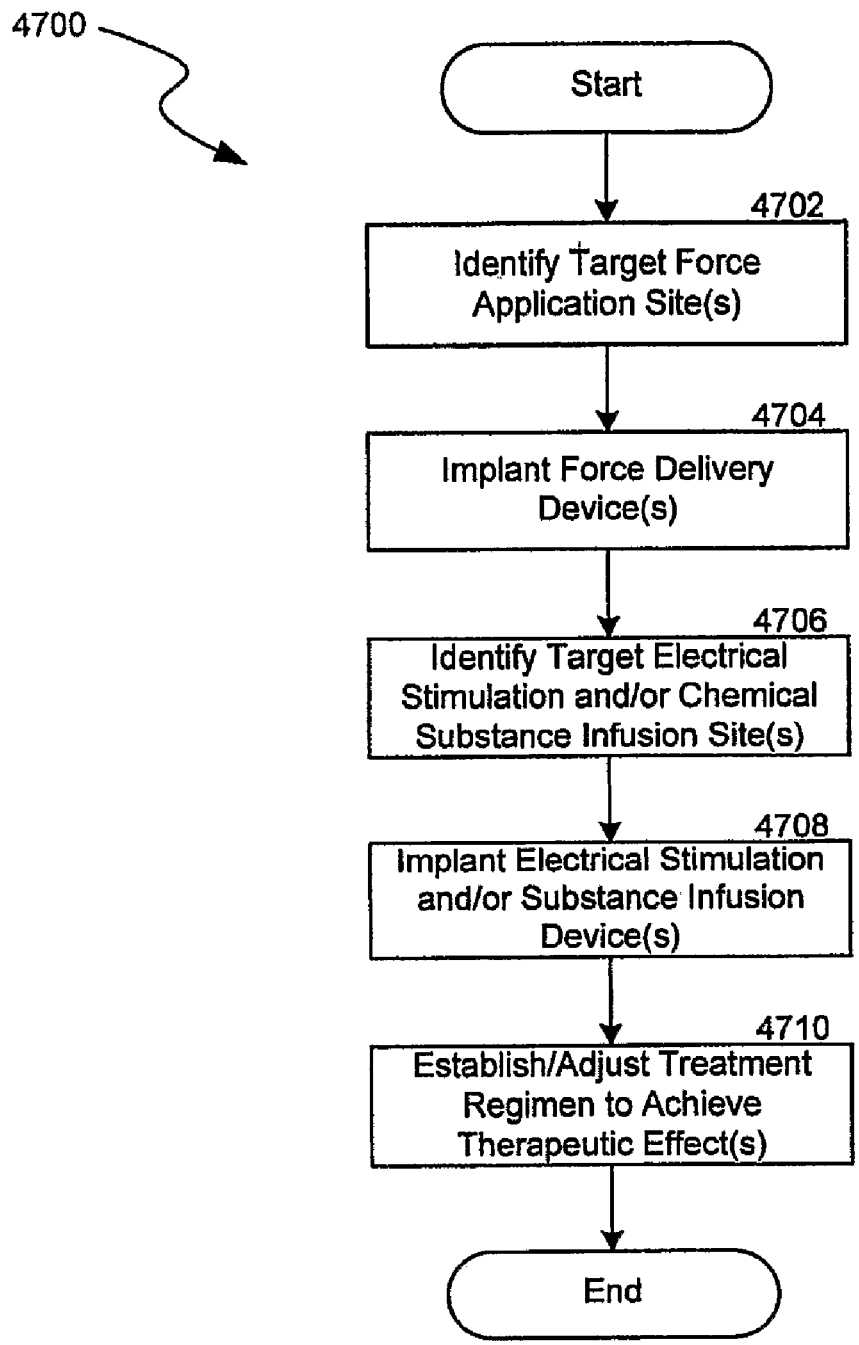
FIG. 47 is a flow diagram illustrating a method for treating a patient with a force delivery device in accordance with an embodiment of the invention.

FIG. 47 illustrates a process 4700 for treating a patient, and includes identifying one or more target force application sites (process portion 4702). The target force application sites may be identified using any of a variety of suitable techniques, including the imaging techniques described previously. In process portion 4704, a force delivery device is implanted at least proximate to the target force application site. Process portion 4706 (which is optional in some cases) includes identifying target electrical stimulation sites and/or chemical substance (drug) infusion sites. As described above, the electrical stimulation sites and the chemical substance infusion sites may be positioned proximate to or remote from the target force application site. In process portion 4708, suitable electrical stimulation and/or drug infusion devices are implanted at the target sites identified in process portion 4706. In process portion 4710, a treatment regimen is established and, optionally, adjusted over the course of time to achieve a therapeutic effect for the patient.

Figure 48:
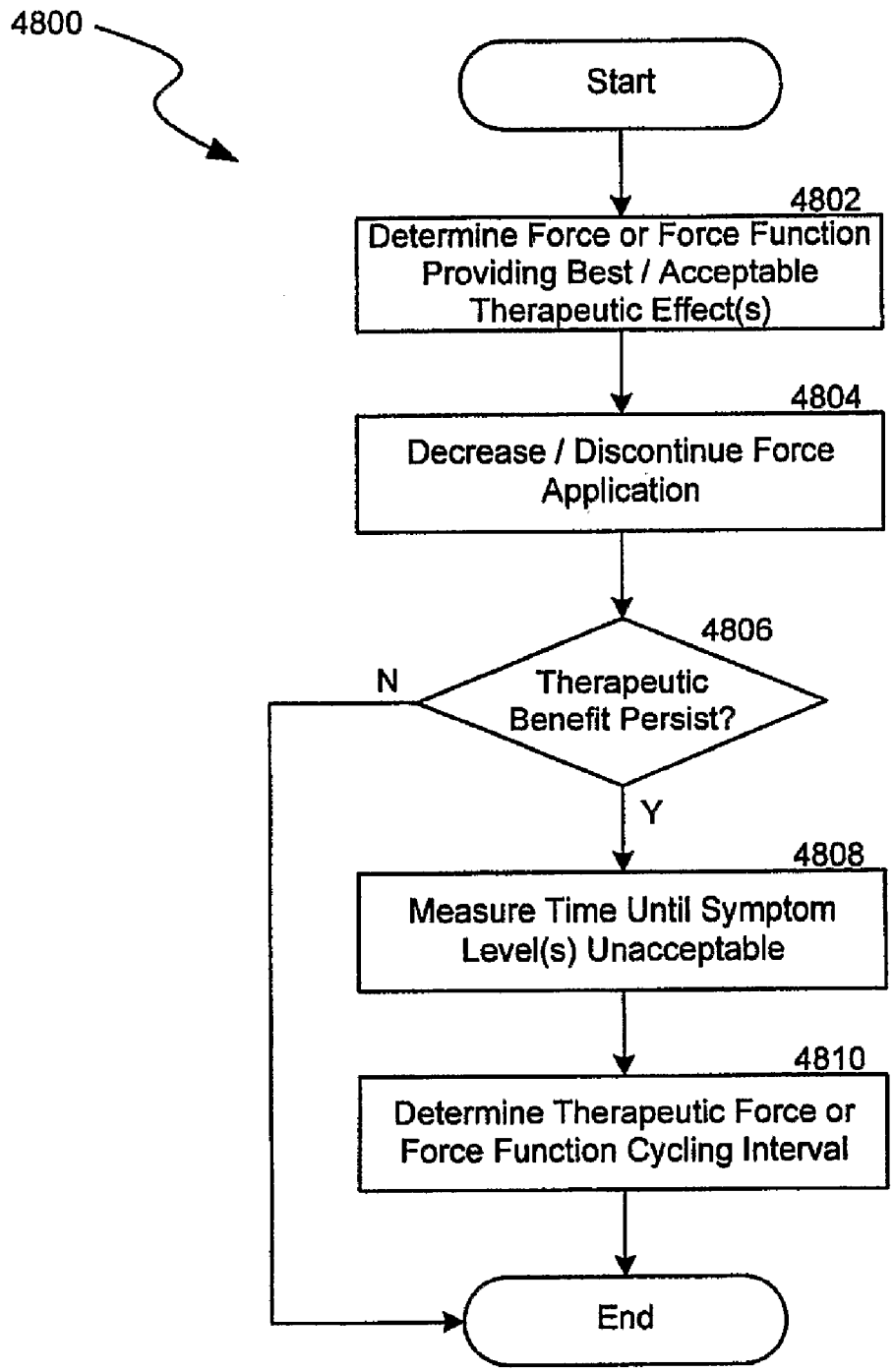
FIG. 48 is a flow diagram illustrating a method for updating the manner in which a mechanical force is delivered to the patient during the course of a treatment regimen in accordance with an embodiment of the invention.

FIG. 48 illustrates a process 4800 for providing treatment to a patient in accordance with another aspect of the invention. Process portion 4802 includes determining a force or force function that provides at least acceptable therapeutic effects for the patient. This force or force function can correspond to the constant or varying force applied by the force delivery device when it is in the first state, as discussed above with reference to FIG. 46. In process portion 4804, the force applied to the patient is decreased or discontinued for a selected time interval (e.g., corresponding to the second state). It is believed that during this low activity or zero activity interval, the therapeutic benefit to the patient can persist. Accordingly, process portion 4806 can include querying whether the therapeutic benefit is persisting. If not, the process can end and optionally can be restarted. If the therapeutic benefit is persisting, then in process portion 4808, the time interval until the patient's symptom levels become unacceptable can be measured. For example, process portion 4808 can include receiving feedback either from the patient directly or from sensors coupled to the patient that indicate when the patient symptoms (e.g., the symptoms that the mechanical force is expected to reduce or eliminate) rise to an unacceptable or other threshold level, after the state of the device has been changed to the second state.

Process portion 4810 can include determining a therapeutic force or force function cycling interval, for example, based upon the results obtained in process portion 4808. In a particular embodiment, the foregoing process may determine that a mechanical force applied to the patient for five minutes may persist for an additional 20 minutes. Accordingly, the force function cycling interval can include five minutes at a particular constant force or force function (e.g., the first state), followed by 20 minutes during which no force or a significantly reduced force is applied (e.g., the second state). This cycle can then be repeated multiple times over the course of a treatment regimen.

Figure 49A:
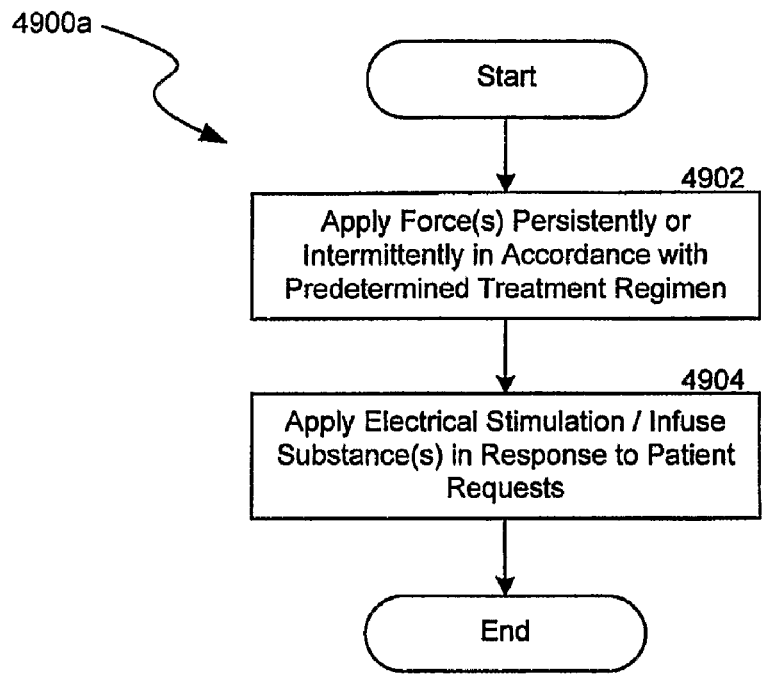
FIGS. 49A and 49B illustrate methods for adjusting treatment regimens in response to patient requests.
Figure 49B:
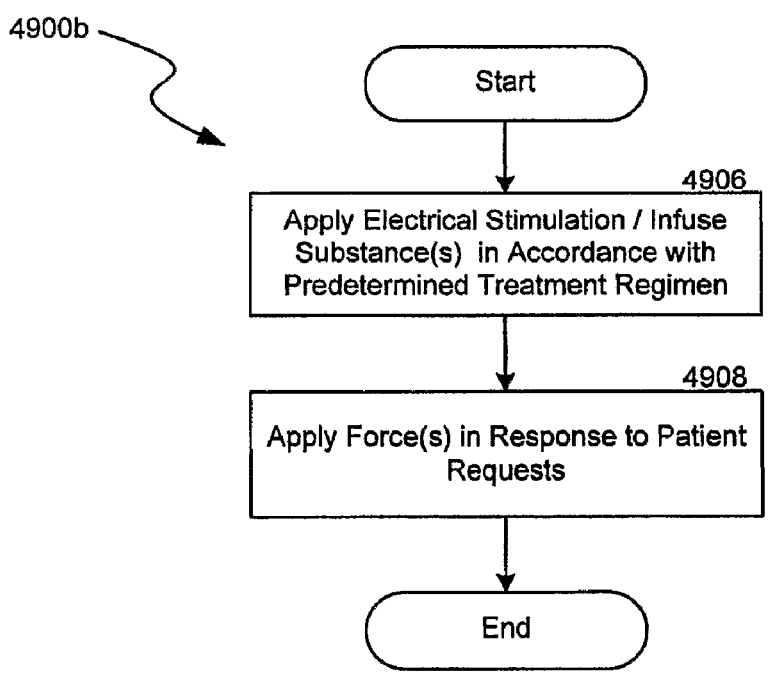

As described above, one or more sensors may be used to automatically determine the effect of the treatment applied to the patient, and may be used in a feedback fashion to effect subsequent treatment. FIGS. 49A and 49B illustrate embodiments in which this feedback is provided when the patient makes an active request, in addition to, or in lieu of the feedback provided by sensors. For example, FIG. 49A illustrates a process 4900a that includes applying one or more forces persistently or intermittently in accordance with a predetermined treatment regimen (process portion 4902). In process portion 4904, electrical stimulation and/or drug infusion is provided in response to a patient request. For example, if the patient finds that during particular intervals, the force application by itself does not provide adequate symptom relief, the patient can request electrical stimulation and/or drug infusion. In another embodiment, the patient can request electrical stimulation and/or drug infusion during intervals when the force delivery device is applying a relatively low force or no force.

FIG. 49B illustrates a process 4900b in which electrical stimulation and/or substance infusions are provided to the patient in accordance with a predetermined treatment regimen (process portion 4906) and the patient can additionally select the application of mechanical force to the neural tissue at the patient's election (process portion 4908) via a patient request. Accordingly, the patient can elect the application of a mechanical force (e.g., from an already-implanted force delivery device) at times when an existing electrical stimulation and/or substance infusion device fail to provide the desired level of relief.

Figure 50:
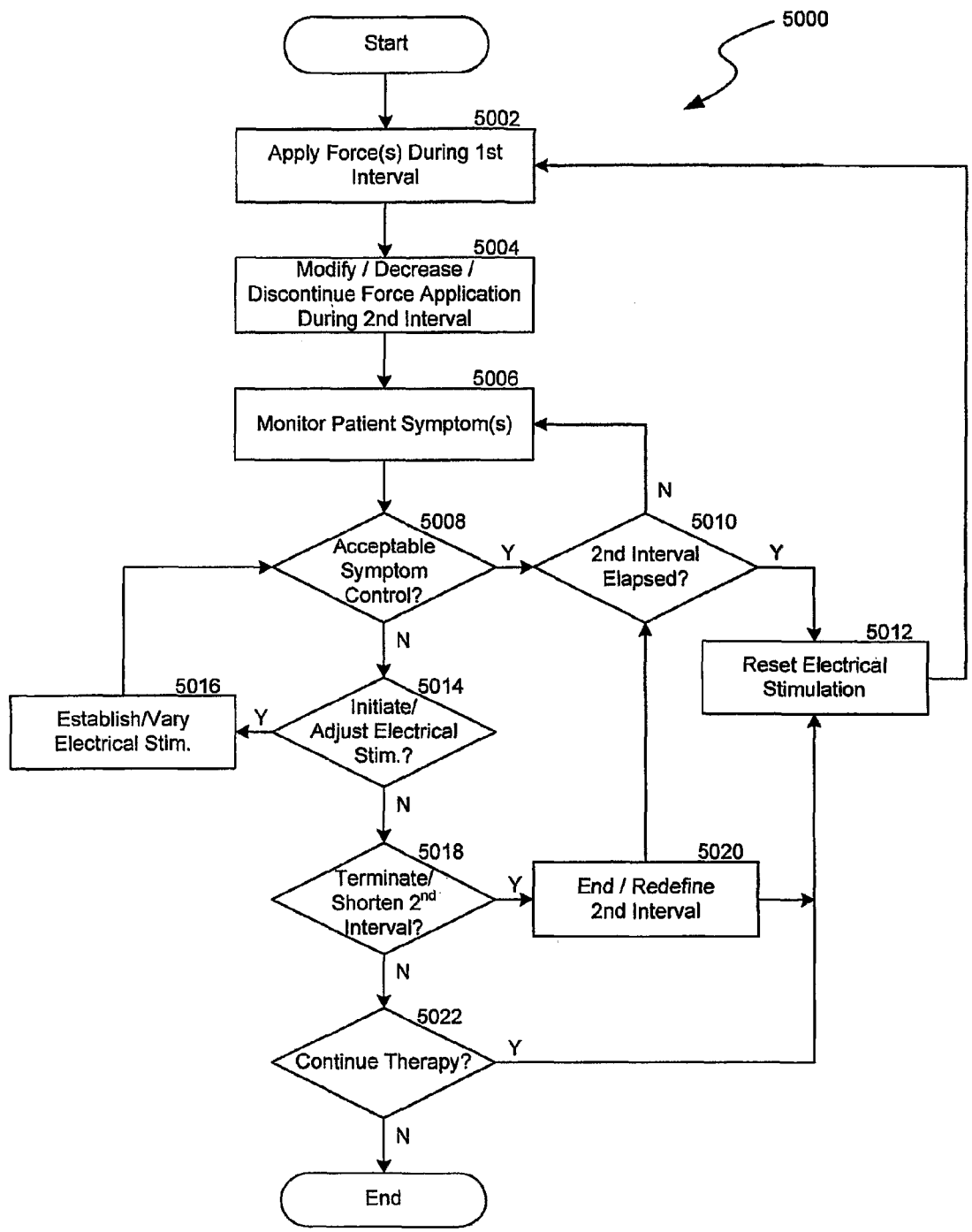
FIG. 50 is a flow diagram illustrating a process for applying force to a patient's neural tissue in accordance with still another embodiment of the invention.

FIG. 50 illustrates a process 5000 for providing electrical stimulation and mechanical force to a patient in accordance with another treatment regimen. Process portion 5002 includes applying one or more forces during a first interval (e.g., a constant force or a scheduled varying force while the force delivery device is in the first state). In process portion 5004, the force is either discontinued, modified or decreased during a second time interval (e.g., while the force delivery device is in the second state). It is expected that during this time interval, the beneficial effects achieved from the force application during the first interval will persist. Accordingly, process portion 5006 can include monitoring the patient symptoms. As part of this process, process portion 5008 can include determining whether an acceptable symptom control has been achieved. If it has, process portion 5010 can include determining whether the second time interval has elapsed. If it has not, the monitoring process continues. If the second time interval has elapsed, an existing electrical stimulation program can be reset (process portion 5012) and the application of forces in accordance with the first interval can be restarted (process portion 5002).

If in process portion 5008, it is determined that acceptable symptom control has not been achieved, then in process portion 5014, it can be determined whether to initiate or adjust electrical stimulation parameters. If it is determined that such an adjustment or initiation is potentially beneficial, then in process portion 5016, the electrical stimulation can be initiated and/or adjusted. If not, then in process portion 5018, it can be determined whether the second interval should be terminated or shortened. If so, process portion 5020 includes ending or redefining the second interval. If the second interval is ended, the treatment program can proceed with process portion 5012, resetting the electrical stimulation. If the second interval has been redefined, the treatment program can return to process portion 5010. If in process portion 5018, it is determined that terminating or shortening the second interval is not expected to be beneficial, then in process portion 5022, it is determined whether the overall therapy program should be continued. If not, the process can end. If so, then the electrical stimulation program can be reset (process portion 5012) and the process can begin again with process portion 5002.

FIG. 51 is a table that includes a list of representative dysfunctions or indications, and corresponding target brain regions. It is expected that the application of an appropriate therapy at the target brain region will have a beneficial effect for a patient suffering from the corresponding dysfunction. The treatment can include the application of mechanical force, and/or the application of a chemical substance (e.g., a drug), and/or the application of electrical stimulation. Any of these treatments can be applied at or near the surface of the target neural structure, or at an intraparenchymal location. It is believed that in at least some instances, the foregoing therapies, singly or in combination, may provide patient benefits that previously have not been available.

From the foregoing, it will be appreciated that specific embodiments of the invention have been described herein for purposes of illustration, but that various modifications may be made without deviating from the scope of the invention. For example, the force delivery device can include force application elements other than and/or in addition to the bladder shown in FIG. 46. The actuator can accordingly also have different arrangements. In some instances when the force delivery device includes a bladder, the bladder can undergo significant changes in shape and/or size as the pressure within it changes. Aspects of the invention described in the context of particular embodiments may be combined or eliminated in other embodiments. For example, the force delivery device shown in FIG. 46 can include force application elements described in previous Figures. While advantages associated with certain embodiments of the invention have been described in the context of those embodiments, other embodiments may also exhibit such advantages, and not all embodiments need necessarily exhibit such advantages to fall within the scope of the invention. Accordingly, the invention is not limited except as by the appended claims.

The invention claimed is:

1. An implantable patient treatment apparatus for implanting in neural tissue, the apparatus comprising:
   an implantable force delivery device that is changeable between a first state in which the force delivery device applies a first mechanical force to the neural tissue, and a second state in which the force delivery device applies no mechanical force or a second mechanical force less than the first mechanical force to the neural tissue while the force delivery device is implanted;
   an actuator coupled to the force delivery device with a communication link to change the state of the force delivery device; and
   a controller operatively coupled to the actuator to automatically direct the force delivery device to change repeatedly between the first and second states while the forte delivery device is implanted,
   wherein the neural tissue is selected from the group consisting of the cortex, subcortical structures, the spinal cord and the peripheral nervous system and wherein the controller and the actuator are configured to direct the force delivery device to apply a maximum constant pressure from about 26.5 gm/cm$^2$ to about 60 gm/cm$^2$.

2. The apparatus of claim 1 wherein the force delivery device applies a changing mechanical force when in the first state, and wherein the force delivery device applies an average mechanical force when in the second state that is less than an average mechanical force applied when in the first state.

3. The apparatus of claim 1 wherein the force delivery device is inflatable to change between the first and second states, wherein the actuator includes a fluid reservoir, and wherein the communication link includes a fluid conduit.

4. The apparatus of claim 1 wherein the controller and the actuator are configured to direct the force delivery device to apply a maximum constant pressure of from about 26.5 gm/cm$^2$ to about 30 gm/cm$^2$.

5. The apparatus of claim 1 wherein the controller and the actuator are configured to direct the force delivery device to apply a maximum intermittent pressure of from about 53 gm/cm$^2$ to about 60 gm/cm$^2$.

6. The apparatus of claim 1 wherein the controller includes a computer-readable medium having instructions for directing the action of the actuator.

7. The apparatus of claim 1 wherein the controller is configured to direct the force delivery device to apply a force in accordance with a consistent schedule on a repeated, intermittent basis.

8. The apparatus of claim 1 wherein the controller is configured to direct the force delivery device to apply a force for periods of time that vary from one period to another.

9. The apparatus of claim 1, further comprising a drug delivery device coupleable to a source of patient drugs and coupled to the controller, wherein the controller is configured to coordinate the change in state of the force delivery device with the application of drugs to the patient.

10. The apparatus of claim 1, further comprising an electrode coupled to a source of electrical potential, the electrode being configured to apply an electrical current to the patient.

11. The apparatus of claim 10 wherein the electrode is carried by the implantable force delivery device.

12. The apparatus of claim 10 wherein the controller is coupled to both the electrode and the actuator, and wherein the controller is configured to direct electrical energy to the electrode at first level when the force delivery device is in the second state, and wherein the controller is configured to direct no electrical energy or electrical energy at a second level less than the first level when the force delivery device is in the first state.

13. The apparatus of claim 1, further comprising an implantable electrode coupled to the controller to provide to the controller a feedback signal indicative of electrical activity in the patient.

14. The apparatus of claim 1, further comprising a feedback sensor coupled to the controller, the feedback sensor being configured to sense a characteristic of the patient, and wherein the controller is configured to receive a signal from the feedback sensor and direct a change in the state of the force delivery device based at least in part on the signal received from the feedback sensor.

15. The apparatus of claim 1, further comprising a patient-controllable feedback device coupled to the controller, and wherein the controller is configured to receive a signal from the feedback device and direct a change in state of the force delivery device based at least in part on the signal received from the feedback device.

16. The apparatus of claim 1 wherein the force delivery device is configured to be implanted at a cortical location.

17. An implantable patient treatment apparatus for implanting in neural tissue, the apparatus comprising:
   implantable force delivery means for applying a mechanical force to neural tissue, the force delivery means being changeable between a first state in which the force delivery means applies a first mechanical force to neural tissue, and a second state in which the force delivery means applies no mechanical force or a second mechanical force less than the first mechanical force to the neural tissue while the force delivery means is implanted;
   actuation means for changing the state of the force delivery means; and
   control means operatively coupled to the actuation means for automatically directing the force delivery means to repeatedly change state while the force delivery means is implanted,
wherein the neural tissue is selected from the group consisting of the cortex, subcortical structures, the spinal cord and the peripheral nervous system and wherein the control means and the actuation means are configured to direct the force delivery means to apply a maximum constant pressure about 26.5 gm/cm$^2$ to about 60 gm/cm$^2$.

18. The apparatus of claim 17 wherein the force delivery means applies a changing mechanical force when in the first state, and wherein the force delivery means applies an average mechanical force when in the second state that is less than an average mechanical force applied when in the first state.

19. The apparatus of claim 17 wherein the force delivery means is inflatable to change between the first and second states, and wherein the actuator means includes a fluid reservoir.

20. The apparatus of claim 17 wherein the control means includes a computer-readable medium having instructions for directing the action of the actuator.

21. The apparatus of claim 17, further comprising an electrode coupled to a source of electrical potential, the electrode being configured to apply an electrical current to the patient.

22. The apparatus of claim 21 wherein the electrode is carried by the implantable force delivery means.

23. A method of eating a patient by effectuating a change in a neural function of the patient, the method comprising:
   directing an implanted force delivery device to repeatedly alternate between a first state and a second state while the force delivery device is implanted in a patient, wherein:
      when the force delivery device is in the first state, it applies a first mechanical force to target neural tissue of the patient; and
      when the force delivery device is in the second state, it applies no mechanical force or a second mechanical force less than the first mechanical force to the target neural tissue over the course of a treatment regimen to achieve a patient benefit, and
      wherein the neural tissue is selected from the group consisting of the cortex, subcortical structures, the spinal cord and the peripheral nervous system.

24. The method of claim 23 wherein the force delivery device applies a changing mechanical force when in the first state, and wherein the force delivery device applies an average mechanical force when in the second state that is less than an average mechanical force applied when in the first state.

25. The method of claim 23, further comprising identifying a target site at which the target neural tissue is located.

26. The method of claim 23, further comprising implanting the force delivery device at least proximate to the target neural tissue.

27. The method of claim 23 wherein directing the force delivery device includes automatically directing the force delivery device.

28. The method of claim 23 wherein directing the force delivery device is carried out by a computer-readable medium.

29. The method of claim 23, further comprising determining whether the patient realizes a therapeutic benefit while the force delivery device applies no mechanical force or a second mechanical force less than the first mechanical force.

30. The method of claim 29, further comprising determining when a patient symptom level meets or exceeds a threshold level.

31. The method of claim 23, further comprising:
   determining when a patient symptom level meets or exceeds a threshold level; and
   changing a characteristic of a manner in which the force delivery device applies a mechanical force to the target neural tissue based at least in part on determining that the patient symptom level meets or exceeds the threshold level.

32. The method of claim 23 wherein directing the force delivery device to apply a first mechanical force to the neural tissue is based at least in part on a contemporaneous patient request.

33. The method of claim 23 wherein directing the force delivery device to apply no mechanical force or a second mechanical force less than the first mechanical force is based at least in part on a contemporaneous patient request.

34. The method of claim 23, further comprising applying electrical stimulation, a drug infusion or both to the patient as part of a treatment regimen that includes the application of the mechanical force.

35. The method of claim 34 wherein applying electrical stimulation, a drug infusion or both is based at least in part on a contemporaneous patient request.

36. The method of claim 34 wherein applying electrical stimulation, a drug infusion or both is carried out at a site spaced apart from the target neural tissue.

37. The method of claim 23, further comprising applying electrical stimulation to the patient as part of a treatment regimen that includes the application of the mechanical force.

38. The method of claim 37 further comprising coordinating changes in the force applied by the force delivery device with changes in the electrical stimulation applied to the patient.

39. The method of claim 23, further comprising selecting the neural tissue to include cortical tissue.

40. The method of claim 23, further comprising selecting the neural tissue to include subdural structures.

41. The method of claim 23, further comprising selecting the neural tissue to include spinal tissue.

42. The method of claim 23, further comprising selecting the neural tissue to include peripheral neural tissue.

43. The method of claim 23 wherein when the force delivery device is in the first state, it applies a mechanical pressure of less than about 30 gm/cm$^2$ for less than 60 minutes.

44. The method of claim 23 wherein when the force delivery device is in the first state, it applies a mechanical pressure of less than 60 gm/cm$^2$ for less than 10 minutes.

45. The method of claim 23 wherein an electrode of the force delivery device contacts the target neural tissue and applies the force.

46. The method of claim 23 wherein directing the implanted force delivery device to repeatedly alternate between a first state and a second state includes directing a change in shape of the force delivery device.

47. The method of claim 23, further comprising automatically sensing a state of the patient and wherein directing the alternation of states of the implanted force delivery device is based at least in part on the sensed state of the patient.

48. A method for treating a patient, comprising:
identifying a patient dysfunction;
identifying a corresponding target location of the brain that is associated with the dysfunction; and
implanting an implantable patient treatment apparatus according to claim 1 at the target location, the therapy including at least one of an electrical stimulation, a chemical infusion, and a mechanical force.

49. The method of claim 48 wherein applying a therapy includes applying an intermittent mechanical force.

50. The method of claim 48 wherein identifying a patient dysfunction includes identifying at least one of schizophrenia and an auditory hallucination, and wherein identifying a target location includes identifying at least one of the cortex and an auditory pathway.

51. The method of claim 48 wherein identifying a patient dysfunction includes identifying Tourette's syndrome, and wherein identifying a target location includes identifying at least one of the motor cortex, the premotor cortex, the supplementary motor cortex, the motor thalamus and the pallidum.

52. The method of claim 48 wherein identifying a patient dysfunction includes identifying at least one of depression and a mood disorder, and wherein identifying a target location includes identifying at least one of the orbital frontal cortex, the prefrontal cortex, and the dorsolateral prefrontal cortex.

53. The method of claim 48 wherein identifying a patient dysfunction includes identifying attention deficit/hyperactivity disorder, and wherein identifying a target location includes identifying at least one of the frontal cortex and the prefrontal cortex.

54. The method of claim 48 wherein identifying a patient dysfunction includes identifying at least one of a substance dependency and an eating disorder, and wherein identifying a target location includes identifying at least one of the following locations: cortical projections to the nucleus accumbens, subcortical projections to the nucleus accumbens, the nucleus accumbens and the ventral tegmental area.

55. The method of claim 18 wherein identifying a patient dysfunction includes identifying a movement disorder including generalized dystonia, focal dystonia, writer cramp, myoclonus, tremor, chorea and hemibalism and wherein identifying a target location includes identifying at least one of the following locations: motor cortex, the premotor cortex, the supplementary motor cortex, the motor thalamus, the motor pallidum, the subthalamic nucleus, the zona incerta and the striatum.

* * * * *